US009909978B2

(12) United States Patent
Ogawa et al.

(10) Patent No.: US 9,909,978 B2
(45) Date of Patent: Mar. 6, 2018

(54) MATURITY DETERMINATION DEVICE AND MATURITY DETERMINATION METHOD

(71) Applicant: Sharp Kabushiki Kaisha, Sakai, Osaka (JP)

(72) Inventors: Rieko Ogawa, Sakai (JP); Takashi Nakano, Sakai (JP); Mitsuru Nakura, Sakai (JP); Daiichiro Nakashima, Sakai (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

(21) Appl. No.: 15/640,616

(22) Filed: Jul. 3, 2017

(65) Prior Publication Data
US 2018/0011008 A1 Jan. 11, 2018

(30) Foreign Application Priority Data
Jul. 5, 2016 (MY) ................................ 2016001261

(51) Int. Cl.
*G01N 21/25* (2006.01)
*G01N 21/31* (2006.01)
(Continued)

(52) U.S. Cl.
CPC ......... *G01N 21/3151* (2013.01); *A01D 46/24* (2013.01); *G01C 11/02* (2013.01); *G01N 33/025* (2013.01)

(58) Field of Classification Search
CPC ........ G01J 3/02; G01J 3/51; G01J 3/28; G01J 3/46; G01N 21/31; G01N 33/02; A01D 46/24; G01C 11/02
See application file for complete search history.

(56) References Cited

U.S. PATENT DOCUMENTS

2009/0268031 A1* 10/2009 Honma ................ A47L 9/00
348/162

FOREIGN PATENT DOCUMENTS

JP         08-122250 A      5/1996
JP      2000-356591 A     12/2000
(Continued)

OTHER PUBLICATIONS

Bensaeed et al., "Oil palm fruit grading using a hyperspectral device and machine learning algorithm", IOP Conf. Series: Earth and Environmental Science 20 (2014), pp. 1-22.

*Primary Examiner* — Abdullahi Nur
(74) *Attorney, Agent, or Firm* — Keating & Bennett, LLP

(57) ABSTRACT

A maturity determination device includes an image capturing device to capture a image including a plurality of first and second pixels; and a signal processing circuit configured to find an area size ratio of an intensity distribution of light of a first wavelength band on the basis of a predetermined reference value based on pixel values obtained from the plurality of first and second pixels, and to generate maturity determination information in accordance with the area size ratio. The first pixel includes a first light transmission filter, and the second pixel includes a second light transmission filter. The intensity of the light of the first wavelength band reflected by the fruits and vegetables varies in accordance with the maturity level, and the intensity of the light of the second wavelength band reflected by the fruits and vegetables is substantially the same regardless of the maturity level.

20 Claims, 23 Drawing Sheets

(51) Int. Cl.
   *G01N 33/02*     (2006.01)
   *G01C 11/02*     (2006.01)
   *A01D 46/24*     (2006.01)

(56) References Cited

FOREIGN PATENT DOCUMENTS

| | | |
|---|---|---|
| JP | 2015-046162 A | 3/2015 |
| WO | 2006/014974 A2 | 2/2006 |
| WO | 2012/074372 A2 | 6/2012 |

* cited by examiner

220A

FIG.9A
(a)
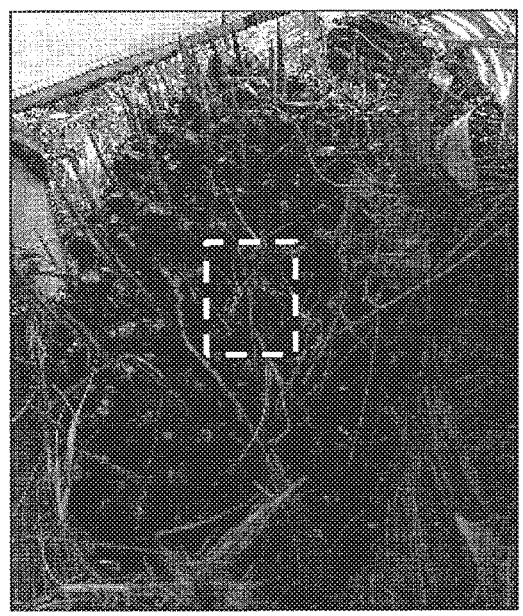
(b)
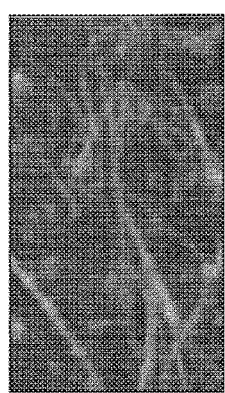
(c)
(d)

FIG.9B
(a)
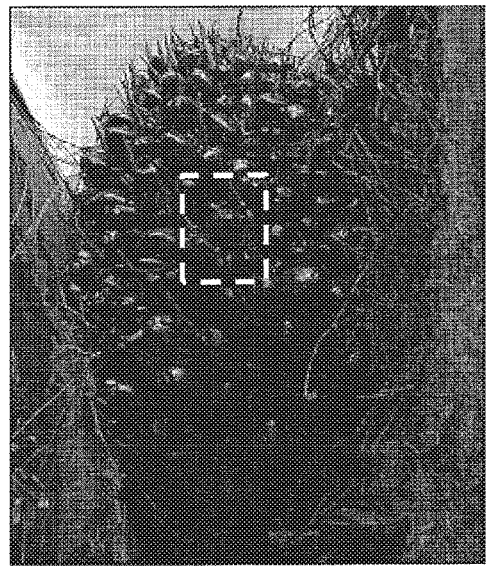
(b) (c) (d)
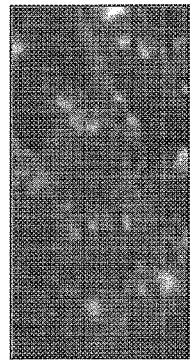  

FIG.9C
(a)
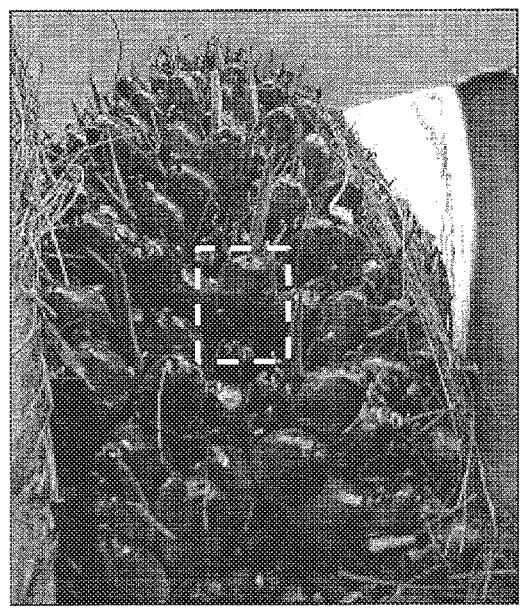
(b)
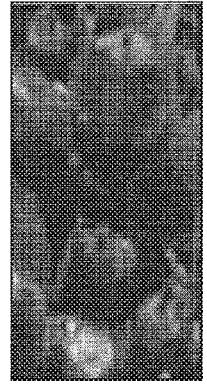
(c)
(d)
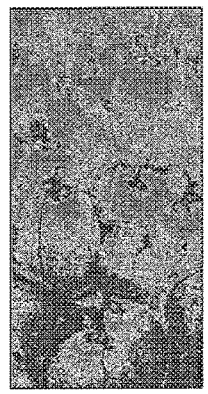

__US 9,909,978 B2__

MATURITY DETERMINATION DEVICE AND MATURITY DETERMINATION METHOD

This application claims priority to Malaysian Patent Application No. PI 2016001261, filed on Jul. 5, 2016, the disclosure of which is hereby incorporated by reference in its entirety.

BACKGROUND OF THE INVENTION

1. Field of the Invention

The present invention relates to a maturity determination device and a maturity determination method.

2. Description of the Related Art

The economic value of a harvesting target of fruits and vegetables depends on the content of a specific ingredient contained in the harvesting target. For example, an oil palm bunch (Fresh Fruit Bunch) includes a large number of (e.g., 1,000 to 3,000) fruits, each of which includes pericarp (also referred to as "pulp"), "mesocarp" and a seed (also referred to as "palm kernel"). In the case where the harvesting target is an oil palm bunch, the content of oil contained in the mesocarp or palm kernel in a fruit is considered important. The oil contained in the mesocarp is generally called "palm oil", and the oil contained in the palm kernel is generally called "palm kernel oil". The oil content of the oil palm fruit is known to be different in accordance with the maturity level of the oil palm bunch (specifically, fruits). Specifically, the oil content of a ripe fruit is known to be higher than the oil content of an unripe, underripe (slightly unripe) or overripe fruit. For example, the oil content of a fruit when being ripe is about three times the oil content thereof when being unripe.

For example, in Malaysia, the Malaysian Palm Oil Board (MPOB) has established guidelines on the maturity level of fruits. Currently, farmers working in oil palm plantations subjectively determine whether or not to harvest the fruits in accordance with the guidelines. As described above, the maturity level of the oil palm bunch significantly influences the amount of yield of oil. Therefore, a wrong subjective determination of a farmer (worker) on whether or not to harvest the fruits may have a significant influence on the amount of yield. In actuality, it is difficult for a farmer to correctly determine whether the fruits are ripe or not, which is a factor that decreases the amount of yield of oil.

In such a situation, measurement devices have been developed for measuring various characteristics of an oil palm bunch, which is a subject (harvesting target), by use of near infrared light without destroying the bunch, namely, in a nondestructive manner. Such measurement devices irradiate the subject with near infrared light of a predetermined wavelength and measure a characteristic to be measured based on the reflectance of the light from the subject.

WO2012/074372 discloses a system that determines the maturity level of oil palm fruits using a hyperspectral imaging technology. WO2012/074372 also discloses the characteristic that the reflectance of the light of the near infrared wavelength band varies in accordance with the maturity level of the fruit. In this system, an image of a harvested oil palm bunch is captured by a spectral camera to acquire a sample image, and the sample image is analyzed based on the characteristic that the reflectance varies in accordance with the maturity level of the fruits to determine the maturity level of the oil palm fruit.

Japanese Laid-Open Patent Publication No. 2000-356591 discloses a nondestructive sugar content meter that calculates the sugar content of fruits and vegetables by a sugar content estimation equation by use of an output from a photoelectric conversion element based on light that has passed a near infrared light wavelength filter. Japanese Laid-Open Patent Publication No. Hei 8-122250 discloses a nondestructive measurement device that determines the maturity level of fruits and vegetables based on the intensity ratio between two specific wavelength components of near infrared light.

SUMMARY OF THE INVENTION

As described above, the economic value of a harvesting target depends on the content of a specific ingredient contained in the harvesting target. Therefore, it is desired to harvest the harvesting target at the time when the content of the specific component in the harvesting target is high. For example, in the case where the harvesting target is an oil palm bunch, it is desired to harvest the oil palm bunch at the time when the content of the palm oil or palm kernel oil is high.

However, the system disclosed in WO2012/074372 is developed for indoor use, and outdoor use is not fully considered. Therefore, the system is of a large scale. In addition, the hyperspectral camera is costly, and thus the system is also costly. In a high-temperature, high-humidity environment, the hyperspectral camera is not considered durable. Therefore, it is very difficult to perform, for example, image capturing of an oil palm bunch in a tree in an oil palm plantation by use of the hyperspectral camera and determine the maturity level on the spot in order to determine an appropriate time to harvest the oil palm bunch. It is now assumed that the time to harvest is determined on the spot by use of the hyperspectral camera and an oil palm bunch having a high economic value is harvested. However, even in such a case, the load on the farmer is increased by the large-scale system, which lowers the efficiency of the entire harvesting work. As a result, the producer does not fully enjoy the advantage that the economic value of the harvesting target is improved.

The present invention made to solve the above-described problem provides a maturity determination device and a maturity determination method determining, with high precision, the time to harvest a harvesting target while reducing the load on a farmer without decreasing the efficiency of the harvesting work.

A maturity determination device in an embodiment according to the present invention is for determining a maturity level of a fruit or vegetable product, and includes an image capturing device including a plurality of pixels arrayed one-dimensionally or two-dimensionally, the image capturing device performing image capturing of at least a part of the fruit or vegetable product to acquire an image, the plurality of pixels including a plurality of first pixels each including a first light transmission filter selectively transmitting light of a first wavelength band and a plurality of second pixels each including a second light transmission filter selectively transmitting light of a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; and a signal processing circuit configured to find an area size ratio of an intensity distribution of the light of the first wavelength band on the basis of a predetermined reference value based on pixel values obtained from the plurality of first pixels and the plurality of second pixels, and to generate maturity determination information in accordance with the area size ratio.

In an embodiment, the first wavelength band may be a wavelength band of near infrared light.

In an embodiment, the first wavelength band may be a wavelength band of near infrared light from 800 nm to 900 nm.

In an embodiment, the second wavelength band may be a wavelength band of blue light.

In an embodiment, the signal processing circuit may divide, on a pixel-by-pixel basis, the pixel values obtained from the plurality of first pixels by the pixel values obtained from the plurality of second pixels associated with the plurality of first pixels; calculate the number of pixels having a quotient value larger than, or equal to, a first threshold value, or a quotient value smaller than, or equal to, the first threshold value, among pixels that are targets of division to find a first ratio of the calculated number of the pixels with respect to the number of the plurality of first pixels; and generate the maturity determination information in accordance with a result of comparing the first ratio against a second threshold value.

In an embodiment, the plurality of pixels may further include a plurality of third pixels each including a third light transmission filter selectively transmitting light of a third wavelength band, the intensity of the light of the third wavelength band reflected by the fruit or vegetable product varying in accordance with the maturity level, the third wavelength band being different from the first wavelength band; and the signal processing circuit may generate the maturity determination information based on pixel values obtained from the plurality of first, second and third pixels.

In an embodiment, the third wavelength band may be a wavelength band of red light.

In an embodiment, the plurality of first, second and third pixels may be associated with each other.

In an embodiment, the signal processing circuit may divide, on a pixel-by-pixel basis, sum values, obtained by adding the pixel values obtained from the plurality of first pixels and the pixel values obtained from the plurality of third pixels on a pixel-by-pixel basis, by the pixel values obtained from the plurality of second pixels; calculate the number of pixels having a quotient value larger than, or equal to, a first threshold value, or a quotient value smaller than, or equal to, the first threshold value, among pixels that are targets of division to find a first ratio of the calculated number of the pixels with respect to the number of the pixels that are the targets of division; and generate the maturity determination information in accordance with a result of comparing the first ratio against a second threshold value.

In an embodiment, the signal processing circuit may divide, on a pixel-by-pixel basis, difference values, obtained by subtracting the pixel values obtained from the plurality of third pixels from the pixel values obtained from the plurality of first pixels on a pixel-by-pixel basis, by the pixel values obtained from the plurality of second pixels; calculate the number of pixels having a quotient value larger than, or equal to, a first threshold value, or a quotient value smaller than, or equal to, the first threshold value, among pixels that are targets of division to find a first ratio of the calculated number of the pixels with respect to the number of the pixels that are the targets of division; and generate the maturity determination information in accordance with a result of comparing the first ratio against a second threshold value.

In an embodiment, the signal processing circuit may divide, on a pixel-by-pixel basis, the pixel values obtained from the plurality of first pixels by the pixel values obtained from the plurality of second pixels; calculate the number of pixels having a quotient value larger than, or equal to, a first threshold value, or a quotient value smaller than, or equal to, the first threshold value, among pixels that are targets of division to find a first ratio of the calculated number of the pixels with respect to the number of the plurality of first pixels; divide, on a pixel-by-pixel basis, the pixel values obtained from the plurality of third pixels by the pixel values obtained from the plurality of second pixels; calculate the number of pixels having a quotient value larger than, or equal to, a second threshold value, or a quotient value smaller than, or equal to, the second threshold value, among the pixels that are the targets of division to find a second ratio of the calculated number of the pixels with respect to the number of the plurality of third pixels; and generate the maturity determination information in accordance with a result of comparing the first ratio against a third threshold value and a result of comparing the second ratio against a fourth threshold value.

In an embodiment, the signal processing circuit may divide, on a pixel-by-pixel basis, the pixel values obtained from the plurality of first pixels by the pixel values obtained from the plurality of second pixels to find a first quotient value, divide, on a pixel-by-pixel basis, the pixel values obtained from the plurality of third pixels by the pixel values obtained from the plurality of second pixels to find a second quotient value, and calculate, on a pixel-by-pixel basis, a third ratio of the second quotient value with respect to the first quotient value; and generate the maturity determination information in accordance with a result of comparing the third ratio against a fifth threshold value.

In an embodiment, the plurality of pixels may further include a plurality of fourth pixels each including a fourth light transmission filter selectively transmitting green light, the second wavelength band being a wavelength band of blue light and the third wavelength band being a wavelength band of red light; and the signal processing circuit may generate a color image based on pixel values obtained from the plurality of second, third and fourth pixels, and generate, based on the maturity determination information, a maturity level image including information on the reference value and representing the maturity level.

In an embodiment, the maturity determination device may further include an output interface outputting the maturity determination information to outside.

In an embodiment, the maturity determination device may further include a driving circuit which generates a driving signal for driving a notification device notifying the maturity level, the notification device being connectable with the maturity determination device, and the driving signal being generated in accordance with the maturity determination information.

In an embodiment, the maturity determination device may further include a notification device which notifies the maturity level; and a driving circuit which generates a driving signal for driving the notification device, the driving signal being generated in accordance with the maturity determination information.

In an embodiment, the notification device may include at least one of an optical device emitting light in accordance with the driving signal, a sound output device outputting a sound in accordance with the driving signal, a vibration device vibrating in accordance with the driving signal, and a display device displaying maturity level information in accordance with the driving signal.

In an embodiment, the maturity determination device may further include a display device; and a driving circuit which generates a driving signal for driving the display device, the driving signal being generated in accordance with the maturity determination information. The display device may display the maturity level image as overlapping the color image in accordance with the driving signal.

In an embodiment, the signal processing circuit may determine whether the fruit or vegetable product is harvestable or not based on the maturity determination information.

In an embodiment, the light reflected by the fruit or vegetable product at the time of harvest thereof may have an optical characteristic that an intensity thereof increases as the light has a longer wavelength in a wavelength band from blue light to near infrared light.

In an embodiment, the fruit or vegetable product may be a bunch with a large number of fruits.

A maturity determination method in an embodiment according to the present invention is for determining a maturity level of a fruit or vegetable product, and includes the steps of receiving an image including at least a part of the fruit or vegetable product, the image including intensity distributions of light of at least a first wavelength band and a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; finding an area size ratio of the intensity distribution of the light of the first wavelength band on the basis of a predetermined reference value in consideration of the intensity distribution of the light of the second wavelength band; and generating maturity determination information in accordance with the area size ratio.

In an embodiment, the first wavelength band may be a wavelength band of near infrared light.

In an embodiment, the first wavelength band may be a wavelength band of near infrared light from 800 nm to 900 nm.

In an embodiment, the second wavelength band may be a wavelength band of blue light.

In an embodiment, in the step of finding the area size ratio, pixel values of the plurality of first pixels that include information representing an intensity distribution of light of the first wavelength band and are included in the image may be divided, on a pixel-by-pixel basis, by pixel values of the plurality of second pixels that are associated with the plurality of first pixels, the plurality of second pixels being included in the image and including information representing an intensity distribution of light of the second wavelength band; and the number of pixels having a quotient value larger than, or equal to, a first threshold value, or a quotient value smaller than, or equal to, the first threshold value, may be calculated among pixels that are targets of division to find a first ratio of the calculated number of the pixels with respect to the number of the plurality of first pixels; and in the step of generating the maturity determination information, the maturity determination information may be generated in accordance with a result of comparing the first ratio against a second threshold value.

In an embodiment, in the step of receiving the image, the image may further include an intensity distribution of light of a third wavelength band, the intensity of the light of the third wavelength band reflected by the fruit or vegetable product varying in accordance with the maturity level, the third wavelength band being different from the first wavelength band; and in the step of generating the maturity determination information, the maturity determination information may be generated based on intensity distributions of the light of the first, second and third wavelength bands.

In an embodiment, the third wavelength band may be a wavelength band of red light.

In an embodiment, the image may include the plurality of first, second and third pixels including information representing the intensity distributions of the light of the first, second and third wavelength bands, the plurality of first, second and third pixels being associated with each other.

In an embodiment, in the step of finding the area size ratio, sum values, obtained by adding the pixel values obtained from the plurality of first pixels and the pixel values obtained from the plurality of third pixels on a pixel-by-pixel basis may be divided, on a pixel-by-pixel basis, by the pixel values obtained from the plurality of second pixels; and the number of pixels having a quotient value larger than, or equal to, a first threshold value, or a quotient value smaller than, or equal to, the first threshold value, may be calculated among pixels that are targets of division to find a first ratio of the calculated number of the pixels with respect to the number of the pixels that are the targets of division; and in the step of generating the maturity determination information, the maturity determination information may be generated in accordance with a result of comparing the first ratio against a second threshold value.

In an embodiment, in the step of finding the area size ratio, difference values, obtained by subtracting the pixel values obtained from the plurality of third pixels from the pixel values obtained from the plurality of first pixels on a pixel-by-pixel basis may be divided, on a pixel-by-pixel basis, by the pixel values obtained from the plurality of second pixels; and the number of pixels having a quotient value larger than, or equal to, a first threshold value, or a quotient value smaller than, or equal to, the first threshold value, may be calculated among pixels that are targets of division to find a first ratio of the calculated number of the pixels with respect to the number of the pixels that are the targets of division; and in the step of generating the maturity determination information, the maturity determination information may be generated in accordance with a result of comparing the first ratio against a second threshold value.

In an embodiment, in the step of finding the area size ratio, the pixel values obtained from the plurality of first pixels may be divided, on a pixel-by-pixel basis, by the pixel values obtained from the plurality of second pixels; the number of pixels having a quotient value larger than, or equal to, a first threshold value, or a quotient value smaller than, or equal to, the first threshold value, may be calculated among pixels that are targets of division to find a first ratio of the calculated number of the pixels with respect to the number of the plurality of first pixels; the pixel values obtained from the plurality of third pixels may be divided, on a pixel-by-pixel basis, by the pixel values obtained from the plurality of second pixels; and the number of pixels having a quotient value larger than, or equal to, a second threshold value, or a quotient value smaller than, or equal to, the second threshold value, may be calculated among the pixels that are the targets of division to find a second ratio of the calculated number of the pixels with respect to the number of the plurality of third pixels; and in the step of generating the maturity determination information, the maturity determination information may be generated in accordance with a result of comparing the first ratio against a third threshold value and a result of comparing the second ratio against a fourth threshold value.

In an embodiment, in the step of finding the area size ratio, the pixel values obtained from the plurality of first pixels may be divided, on a pixel-by-pixel basis, by the pixel values obtained from the plurality of second pixels to acquire a first quotient value; the pixel values obtained from the plurality of third pixels may be divided, on a pixel-by-pixel basis, by the pixel values obtained from the plurality of second pixels to acquire a second quotient value; and a third ratio of the second quotient value with respect to the first quotient value may be calculated on a pixel-by-pixel basis; and in the step of generating the maturity determination information, the maturity determination information may be generated in accordance with a result of comparing the third ratio against a fifth threshold value.

In an embodiment, in the step of receiving the image, the image may further include an intensity distribution of green light, the second wavelength band being a wavelength band of blue light and the third wavelength band being a wavelength band of red light; and the method may further comprise the step of generating a color image based on pixel values obtained from the plurality of second, third and fourth pixels, and generating, based on the maturity determination information, a maturity level image including information on the reference value and representing the maturity level.

In an embodiment, the method may further comprise the step of outputting the maturity determination information to outside.

In an embodiment, the method may further comprise the step of generating a driving signal for driving a notification device notifying the maturity level, the driving signal being generated in accordance with the maturity determination information.

In an embodiment, the notification device may include at least one of an optical device emitting light in accordance with the driving signal, a sound output device outputting a sound in accordance with the driving signal, a vibration device vibrating in accordance with the driving signal, and a display device displaying maturity level information in accordance with the driving signal.

In an embodiment, the method may further comprise the step of displaying the maturity level image as overlapping the color image on a display device.

In an embodiment, the method may further comprise the step of performing image capturing of at least a part of the fruit or vegetable product to acquire the image.

In an embodiment, in the step of acquiring the image, the image may be acquired by performing image capturing of a central part and the vicinity thereof of the fruit or vegetable product.

In an embodiment, in the step of acquiring the image, the image may be acquired a plurality of times.

In an embodiment, the method may further comprise the step of determining whether the fruit or vegetable product is harvestable or not based on the maturity determination information.

In an embodiment, the light reflected by the fruit or vegetable product at the time of harvest thereof may have an optical characteristic that an intensity thereof increases as the light has a longer wavelength in a wavelength band from blue light to near infrared light.

In an embodiment, the fruit or vegetable product may be a bunch with a large number of fruits.

A computer program in an embodiment according to the present invention causes a computer, usable for a maturity determination device determining a maturity level of a fruit or vegetable product, to execute the steps of receiving an image including at least a part of the fruit or vegetable product, the image including intensity distributions of light of at least a first wavelength band and a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; finding an area size ratio of the intensity distribution of the light of the first wavelength band on the basis of a predetermined reference value in consideration of the intensity distribution of the light of the second wavelength band; and generating maturity determination information in accordance with the area size ratio.

According to an embodiment of the present invention, a maturity determination device and a maturity determination method determining, with high precision, the time to harvest a harvesting target while reducing the load on a farmer without decreasing the efficiency of the harvesting work are provided.

BRIEF DESCRIPTION OF THE DRAWINGS

FIG. 9A shows an image I of the unripe bunch F and a mapping image obtained as a result of mapping performed based on the pixel value NIRS of a plurality of first pixels in the image I.

FIG. 9B shows an image I of the underripe bunch F and a mapping image obtained as a result of mapping performed based on the pixel value NIRS of a plurality of first pixels in the image I.

FIG. 9C shows an image I of the ripe bunch F and a mapping image obtained as a result of mapping performed based on the pixel value NIRS of a plurality of first pixels in the image I.

DETAILED DESCRIPTION OF PREFERRED EMBODIMENTS

Figure 1:
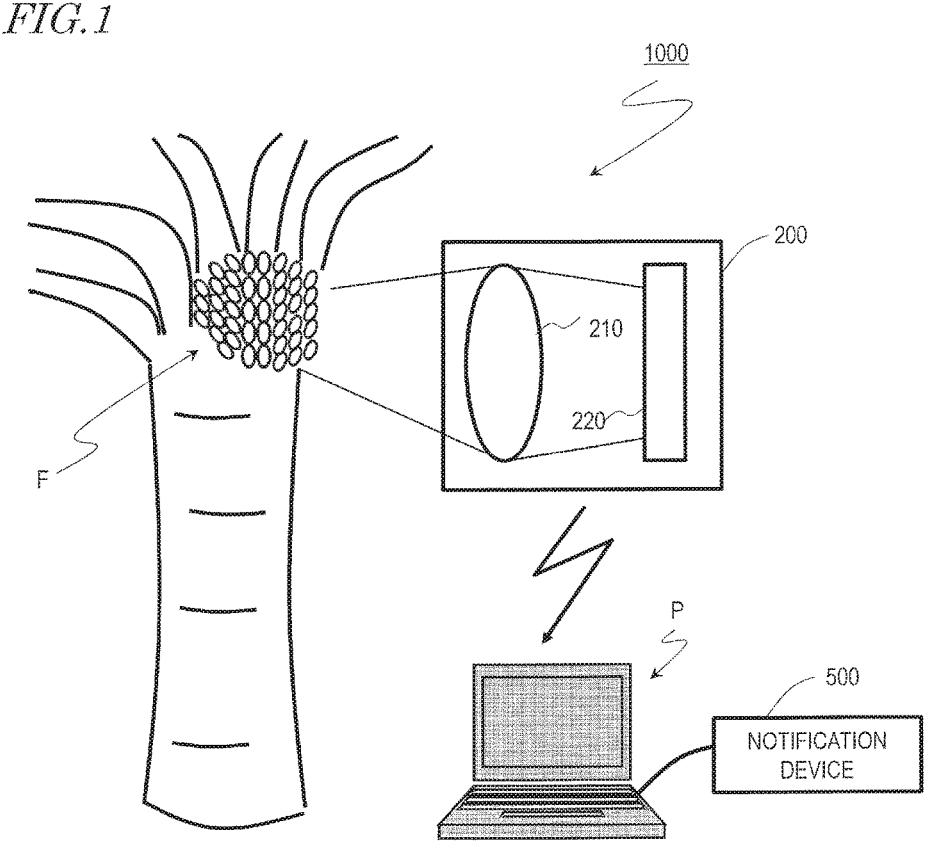
FIG. 1 is a structural view of an example of system 1000 with which a determination method in embodiment 1 is usable.

As a result of accumulating studies, the present inventors found the following problems.

There are problems to be solved in order to determine, highly precisely, the time to harvest of a harvesting target. Oil palm is harvested in units of bunches each including a larger number of fruits. There is a distribution of maturity level of fruits included in one bunch, which is one factor that makes it difficult to determine the maturity level. In the case where one bunch, which is a unit of harvesting, includes a large number of fruits as in the case of oil palm, the maturity level cannot be determined by simply averaging pixel values of a plurality of pixels included in an image of the bunch. One bunch includes dead calyx and leaves in addition to the fruits, which is also a factor that makes it difficult to determine the maturity level. The image of the bunch may include information on the dead calyx and the leaves, which is not related to the fruits. Therefore, it is difficult to use only the information on the fruits to determine the maturity level.

Based on the above-described knowledge, the present inventors found a method by which the maturity level is determined highly precisely even in the case where a bunch includes a large number of fruits having different maturity levels and also includes dead calyx and leaves as in the case of oil palm, and thus have arrived at the present invention.

A maturity determination device in an embodiment according to the present invention determines a maturity level of a fruit or vegetable product and is preferably usable as a device determining a maturity level of, for example, an oil palm bunch including a larger number of fruits. The maturity determination device includes an image capturing device including a plurality of pixels arrayed one-dimensionally or two-dimensionally, the image capturing device performing image capturing of at least a part of the fruit or vegetable product to acquire an image, the plurality of pixels including a plurality of first pixels each including a first light transmission filter selectively transmitting light of a first wavelength band and a plurality of second pixels each including a second light transmission filter selectively transmitting light of a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; and a signal processing circuit configured to find an area size ratio of an intensity distribution of the light of the first wavelength band on the basis of a predetermined reference value based on pixel values obtained from the plurality of first pixels and the plurality of second pixels, and to generate maturity determination information in accordance with the area size ratio. The light of the first wavelength band is typically near infrared light, and the light of the second wavelength band is typically blue. With this structure, the maturity level of a fruit or vegetable product is determined with high precision with the influence of the sunlight being suppressed.

A method in an embodiment according to the present invention determines a maturity level of a fruit or vegetable product and is preferably usable as a method determining a maturity level of, for example, an oil palm bunch including a larger number of fruits. The method includes the steps of receiving an image including at least a part of the fruit or vegetable product, the image including intensity distributions of light of at least a first wavelength band and a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; finding an area size ratio of the intensity distribution of the light of the first wavelength band on the basis of a predetermined reference value in consideration of the intensity distribution of the light of the second wavelength band; and generating maturity determination information in accordance with the area size ratio. The light of the first wavelength band is typically near infrared light, and the light of the second wavelength band is typically blue. With this method, the maturity level of a fruit or vegetable product is determined with high precision with the influence of the sunlight being suppressed.

In this specification, a maturity determination device and a maturity determination method determining the maturity level of an oil palm bunch, which is an example of fruit or vegetable product. In this specification, any type or any part of fruit or vegetable that is to be harvested is referred to as a "fruit or vegetable product". As described below, the present invention encompasses determination of the maturity level of a fruit or vegetable product with which the reflectance of light varies in accordance with the maturity level in a specific wavelength band, for example, coffee fruits, apples and mangoes.

Hereinafter, a maturity determination device and a maturity determination method in embodiments according to the present invention will be described with reference to the attached drawings. In the following description, identical or similar elements will bear the identical reference signs to each other. The maturity determination device and the maturity determination method in an embodiment according to the present invention are not limited to those in any of the following embodiments. For example, one embodiment and another embodiment may be combined together.

Embodiment 1

With reference to FIG. 1 through FIG. 12B, a method for determining the maturity level of an oil palm bunch F (hereinafter, referred to as "determination method") in this embodiment will be described.

[Structure of System 1000 for which the Determination Method is Usable]

An example of structure of a system 1000 for which the determination method in this embodiment is usable will be described. The determination method in this embodiment may also be preferably usable for another device (or a system) different from the system 1000. A specific example of another device (in this specification, will be referred to as a "maturity determination device") will be described below in detail.

FIG. 1 shows an example of structure of the system 1000 for which the determination method in this embodiment is usable. The system 1000 typically includes an image capturing device 200, a calculation device P and a notification device 500. In the system 1000, the image capturing device 200 performs image capturing of at least a part of a large number of fruits in an oil palm bunch (hereinafter, referred to simply as the "bunch") F to acquire an image of the fruits. In this case, it is preferable that the image is of at least three fruits. The calculation device P analyzes the image to generate maturity determination information indicating the maturity level of the bunch F. For example, the notification device 500 notifies a farmer of whether the bunch F is ripe or not in accordance with the maturity determination information.

The image capturing device 200 includes a lens 210 and an image sensor 220. The image capturing device 200 may be realized as, for example, a camera module.

The lens (or lens group) 210 collects light from the bunch F onto an image capturing surface of the image sensor 220. The lens 210 may be a single lens or include a plurality of lenses. The lens 210 may include a lens for autofocus (AF) and/or a lens for optical zooming. The lens for AF and the lens for optical zooming are drivable by a dedicated driver (not shown). The image capturing device 200 may include a control circuit (not shown) controlling such a driver.

The image sensor 220 is, for example, a CCD (Charge Coupled Device) sensor or a CMOS (Complementary Metal Oxide Semiconductor) sensor. The image sensor 220 includes a plurality of pixels arrayed one-dimensionally or two-dimensionally (pixel array 220A shown in FIG. 2). In the case where the plurality of pixels are arrayed one-dimensionally, the image sensor 220 may be a line sensor.

Figure 2:
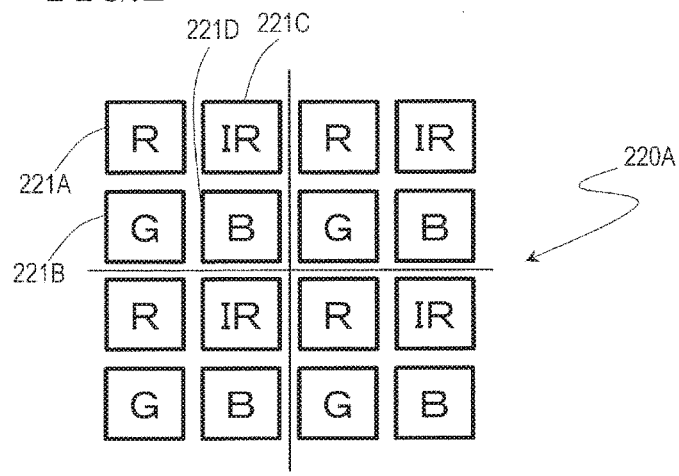
FIG. 2 is a schematic view of pixels of a pixel unit arrayed in four rows by four columns among a plurality of pixels 221 arrayed two-dimensionally in a pixel array 220A.
Figure 3:
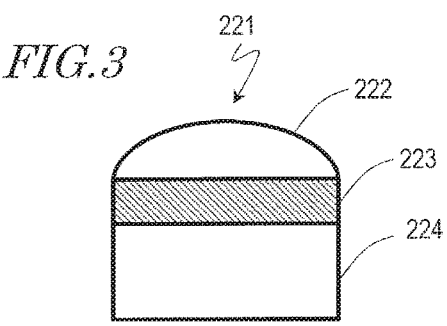
FIG. 3 is a schematic view showing a cross-section of the pixel 221 that is parallel to an optical axis of a microlens 222.
Figure 4:
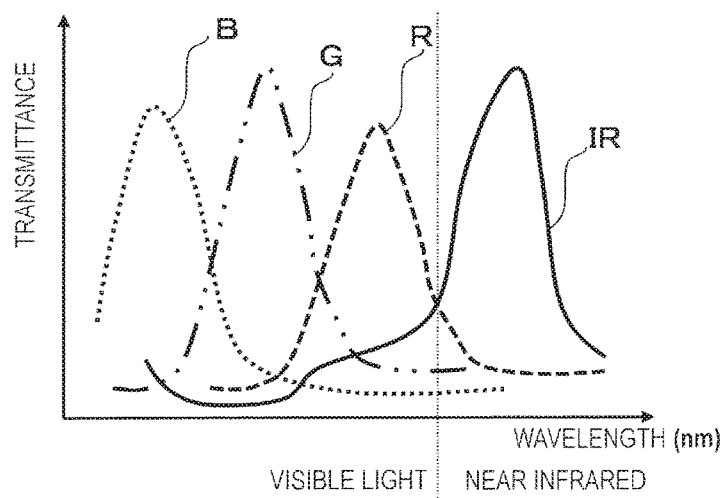
FIG. 4 is a graph showing the light transmission characteristic of a light transmission filter 223.

FIG. 2 shows a part of a plurality of pixels 221 arrayed two-dimensionally in the pixel array 220A, more specifically, the pixels 221 arrayed in four rows by four columns. FIG. 3 schematically shows a cross-section of the pixel 221 that is parallel to an optical axis of a microlens 222. FIG. 4 shows a light transmission characteristic of a light transmission filter 223. In the graph of FIG. 4, the horizontal axis represents the wavelength (nm) of the light, and the vertical axis represents the transmittance of the light transmission filter.

The image sensor 220 includes the plurality of pixels 221 arrayed two-dimensionally (pixel array 220A). The pixels 221 each include the microlens 222, the light transmission filter 223 and a photoelectric conversion element 224.

The microlens 222 is located on the light transmission filter 223, and collects light from the bunch F to improve the pixel sensitivity. The light transmission filter 223 selectively transmits light of a specific wavelength band. For example, the light transmission filter 223 is either an IR filter or one of RGB color filters. As shown in FIG. 4, the IR filter selectively transmits light of a near infrared wavelength band (e.g., 800 nm to 2500 nm), and preferably selectively transmits light of a wavelength band of 800 nm to 900 nm. An R filter selectively transmits light of a red wavelength band (e.g., 620 nm to 750 nm). A G filter selectively transmits light of a green wavelength band (e.g., 500 nm to 570 nm). A blue filter selectively transmits light of a blue wavelength band (e.g., 450 nm to 500 nm).

The photoelectric conversion element 224 is typically a photodiode (PD), and converts received light into an electric signal. The PD is, for example, embedded in a semiconductor substrate formed of silicon (not shown).

As shown in FIG. 2, the pixel array 220A has pixel units each including pixels 221A, 221B, 221C and 221D arrayed in two rows by two columns. The pixels 221A, 221B, 221C and 221D respectively include an R filter, a G filter, an IR filter and a B filter. Such an array corresponds to an array obtained as a result of a G filter in an odd or even number column of a Bayer array being replaced with an IR filter. In this specification, the pixels 221A, 221B, 221C and 221D included in one pixel unit are associated with each other. As described below, pixel values of the pixels associated with each other (e.g., pixels 221A, and 221C) may be subjected to addition, subtraction or division.

Figure 5:
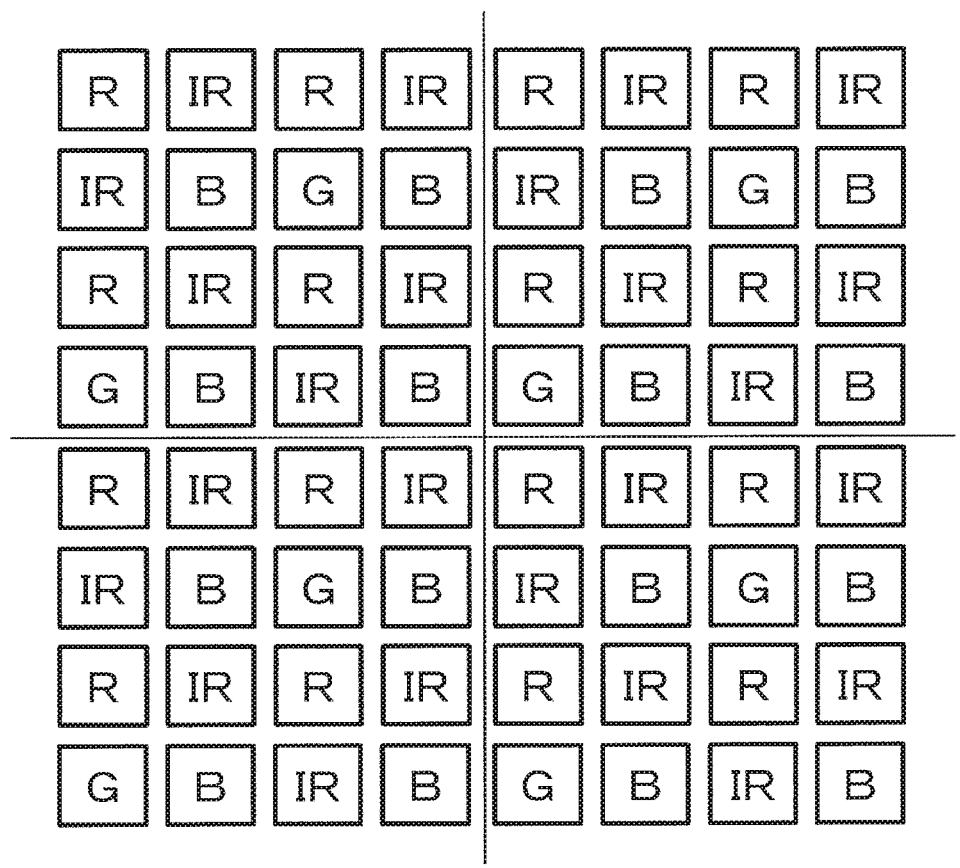
FIG. 5 is a schematic view showing a structure of another pixel unit in the pixel array 220A.

FIG. 5 shows a structure of other pixel units in the pixel array 220A. FIG. 5 shows a part of the plurality of pixels 221 arrayed two-dimensionally in the pixel array 220A, more specifically, the pixels 221 arrayed in eight rows by eight columns. The pixel array 220A may include pixel units each including the pixels 221 arrayed in four rows by four columns. In this example, in each pixel unit, the number of the G filters is smallest and the number of the IR filters is largest. A reason for this is that in the determination method in this embodiment, the pixel value obtained from the pixel 221C including the IR filter is considered most important and the pixel value obtained from the pixel 221B including the G filter is not used.

Any of various pixel unit patterns other than the above-described pixel unit patterns may be selected. For example, the pixel unit may include only the IR filter and the B filter among the above-described plurality of filters. The number of each type of filters included in the pixel unit may be arbitrary.

As described below in detail, the reflectance of light (intensity of reflected light) of a first wavelength band from, for example, the bunch F varies in accordance with the maturity level. The first wavelength band is, for example, a wavelength band of near infrared light. The reflectance of light of a second wavelength band does not vary almost at all in accordance with the maturity level. The second wavelength band is, for example, a wavelength band of blue light. In the case where the maturity level of a fruit or vegetable product exhibiting such a characteristic is to be found, the unit pixel merely needs to include at least the IR filter and the B filter. For example, the two of the filters in the pixel unit shown in FIG. 2 may be the IR filters and the other two filters may be the B filters. Even in such a case, the determination method in this embodiment is usable. However, as described below, it is preferable that the unit pixel includes the RGB filters from the point of view of generating a color image.

In this specification, the term "pixel value" is, for example, an 8-bit gray scale value, and mainly refers to RAW data. The image capturing device 200 at least outputs RAW data.

Alternatively, the image capturing device 200 may have a function of generating a luminance/color difference signal based on the RAW data and outputting the luminance/color difference signal.

The calculation device P includes a signal processing circuit (not shown) that processes pixel values output from the image capturing device 200 to generate maturity determination information. The calculation device P is, for example, a personal computer (PC) such as a laptop computer or the like. Data transmission between the calculation device P and the image capturing device 200 may be performed by, for example, wireless communication. The wireless communication may be conformed to, for example, the Bluetooth (registered trademark) standards. Needless to say, the calculation device P and the image capturing device 200 may be connected with each other in a wired manner by, for example, a USB cable or the like. The calculation device P may further include a driving circuit (not shown) that generates a driving signal for driving the notification device 500 in accordance with the maturity determination information. All of, or a part of, these functions may be implemented on the notification device 500.

The calculation device P may have a function of performing a process generally performed for image processing, for example, gamma correction, color interpolation, spatial interpolation, and auto-white balance.

The notification device 500 notifies the farmer of the maturity level of the bunch F or whether the bunch F is harvestable or not. The notification device 500 is connected with the calculation device P in a wired or wireless manner. The notification device 500 includes at least one of an optical device emitting light in accordance with a driving signal, a sound output device outputting a sound in accordance with the driving signal, a vibration device vibrating in accordance with the driving signal, and a display device displaying maturity information in accordance with the driving signal. The optical device is, for example, an LED (Light Emitting Diode) lamp. The sound output device is, for example, a speaker. The vibration device is, for example, a vibrator. The display device is, for example, a liquid crystal display or an organic EL (Electroluminescence) display.

[Processing Procedure of the Determination Method]

Figure 6:
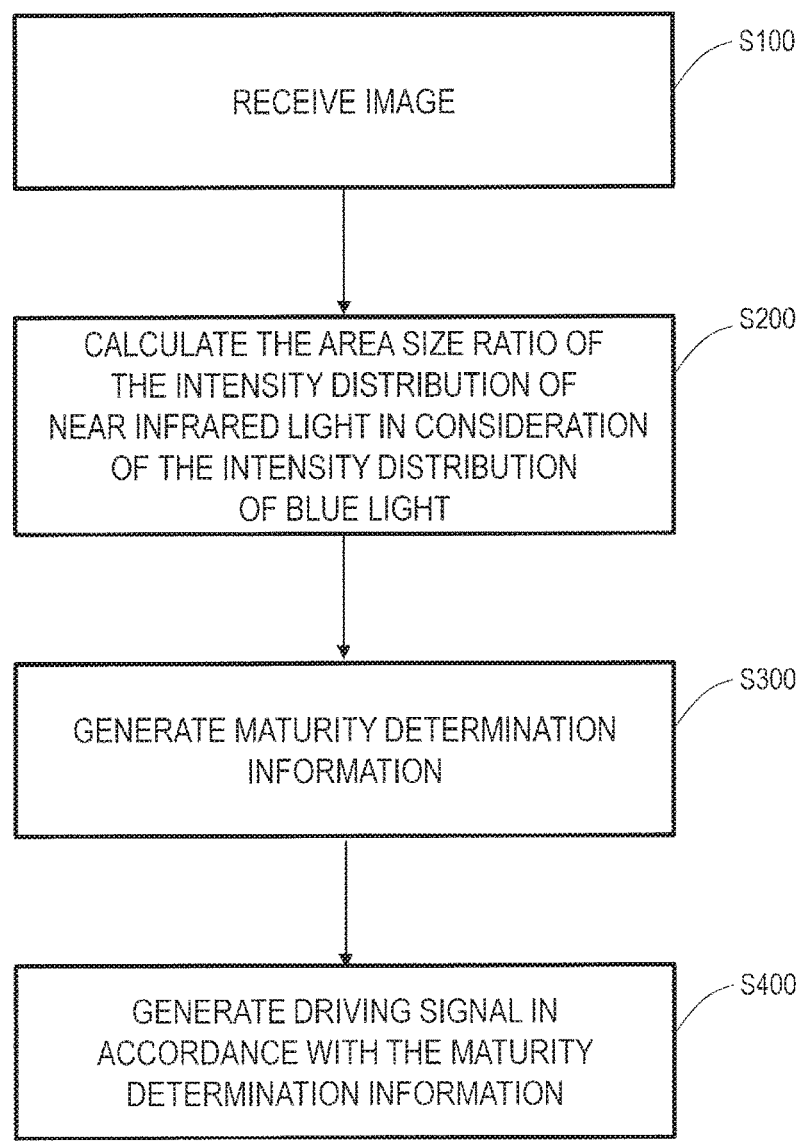
FIG. 6 is a flowchart showing an example of processing procedure of the determination method in embodiment 1.

FIG. 6 shows an example of processing procedure of the determination method in this embodiment. Hereinafter, a method for determining the maturity level of the bunch F in accordance with the processing procedure shown in FIG. 6 by use of the system 1000 will be described. The operating subject executing each of steps is the calculation device P, specifically, a signal processing circuit or a driving circuit of the calculation device P.

(Step S100)

The image capturing device 200 performs image capturing of all of, or a part of, the large number of fruits in the bunch F (preferably, at least three fruits) to acquire an image I. As described below, the image capturing device 200 may perform image capturing of the entirety of the oil palm tree. The image capturing device 200 may acquire the image I by performing image capturing of a central part and the vicinity thereof of the bunch F. Moreover, the image capturing device 200 preferably acquires the image I through image capturing of a well-sunlit portion of the bunch F, e.g., a tip thereof. The reason is that, presumably, the fruits in a sunlit portion of the bunch F will be the first to start maturing.

The image capturing device 200 may perform the image capturing a plurality of times to acquire the image I a plurality of times. The acquired pieces of image data may be added together to improve the SN ratio. The acquired image I includes intensity distributions of near infrared light and blue light reflected by the bunch F. In this embodiment, the image I includes intensity distributions of the near infrared light, red light, green light and blue light reflected by the bunch F. In other words, the image I includes pixel values (image data) REDS, GLNS, NIRS and BLUS obtained from the four pixels 221A, 221B, 221C and 221D. In the embodiments of the present invention, the image I merely needs to include at least the intensity distributions of the near infrared light and the blue light.

In step S100, the calculation device P receives the image I from the image capturing device 200. The operation of "receiving the image" encompasses acquiring the image I in real time when the image capturing device 200 acquires the image I. The operation of "receiving the image" is not limited to this. For example, the calculation device P may acquire the image I later by reading the image I stored on a storage medium such as an external hard disc HD or the like connected with the calculation device P. Such an operation may be encompassed in the operation of "receiving the image".

Figure 7:
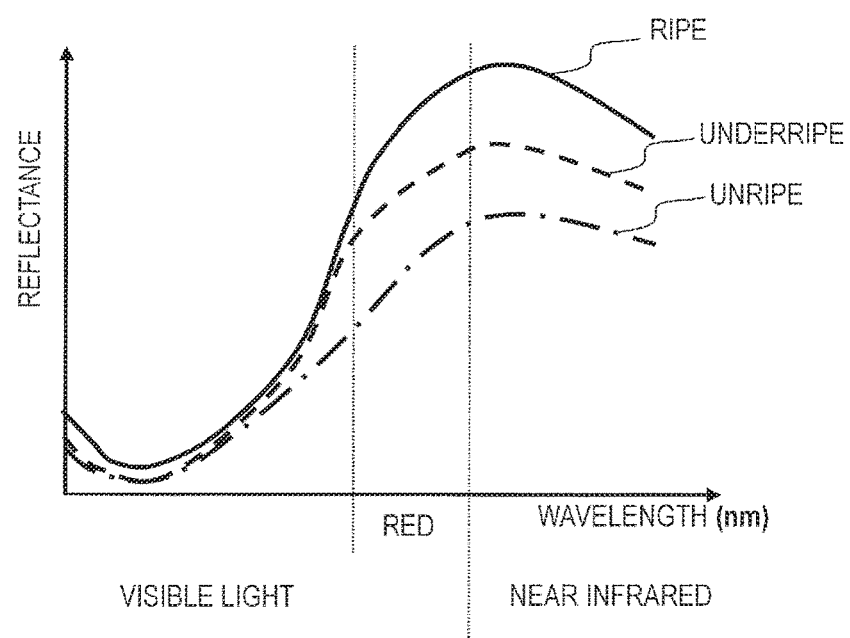
FIG. 7 is a graph schematically showing how the intensity of the reflected light (reflectance) varies in accordance with the maturity level at the time of harvest of a bunch F.

FIG. 7 schematically shows how the intensity of the reflected light (reflectance) varies in accordance with the maturity level at the time of harvest of the bunch F. The horizontal axis represents the wavelength of the light (nm), and the vertical axis represents the reflectance. In general, the image sensor 220 (e.g., image sensor using silicon) has a sensitivity characteristic depending on the wavelength of the light. Generally, for measuring the reflectance in consideration of the sensitivity characteristic, the pixel value that is output from the image sensor 220 is standardized by use of a standard white plate. The standard white plate is a highly reflective diffuse reflection plate that generates diffuse reflection light not depending on the angle. The reflectance represented by the vertical axis of FIG. 7 shows the ratio of the reflectance from the bunch F with respect to the reflectance measured by use of the standard white plate.

The maturity may be classified into, for example, "ripe", "underripe" and "unripe". Needless to say, the maturity may be classified into a larger number of categories. For example, the category "overripe" may be provided. A category representing another maturity level (e.g., "slightly ripe" may be provided between "ripe" and "underripe". At the time of harvest of the oil palm bunch F, the light reflected by the bunch F has a reflectance characteristic that the intensity increases as the light has a longer wavelength within the wavelength band from the blue light to the near infrared light. Especially in a wavelength band of the red light, which is visible light, the reflectance characteristic is exhibited that the intensity increases as the maturity level of the bunch F rises. Also in the near infrared light wavelength band having the maximum wavelength of the reflected light that may be received in accordance with the sensitivity characteristic of the image sensor 220, the reflectance characteristic is exhibited that the intensity increases as the maturity level of the bunch F rises. As can be seen, especially in the wavelength band from the red light to the near infrared light, the reflectance is represented by a curve unique to the maturity level. What should be paid attention is that the light reflected by the bunch F of the blue wavelength band has generally the same intensity regardless of the maturity level. In other words, the reflectance does not vary almost at all in accordance with the maturity level. As described below in detail, an appropriate threshold value for the reflectance may be set in each wavelength band based on such characteristics and the reflectance and the threshold value may be compared against each other, so that the maturity level is determined.

In this embodiment according to the present invention, the image I including the intensity distributions of at least the near infrared light and the blue light may be analyzed, so that the maturity level is determined. In this embodiment, the maturity level is determined based on the pixel values NIRS and BLUS. Therefore, for example, the pixel unit including the pixels 221 in two rows by two columns shown FIG. 2 includes at least a pixel 221C including the IR filter and a pixel 221D including the B filter. The pixel unit including the pixels 221 in two rows by two columns may include, for example, two pixels 221C and two pixels 221D. As described below in detail, the image I may also be analyzed by further use of the pixel value REDS. This allows the maturity level to be determined with higher precision. In this case, the image I includes the intensity distributions of at least the near infrared light, the red light and the blue light.

(Step S200)

The calculation device P calculates an area size ratio of the intensity distribution of the near infrared light in the received image I in consideration of the intensity distribution of the blue light. The image I includes a plurality of first pixels (or image data) including information representing the intensity distribution of the near infrared light, a plurality of second pixels including information representing an intensity distribution of the blue light, a plurality of third pixels including information representing an intensity distribution of the red light, and a plurality of fourth pixels including information representing an intensity distribution of the green light. As described above, the image I merely needs to include at least the plurality of first pixels and the plurality of second pixels.

Figure 8:
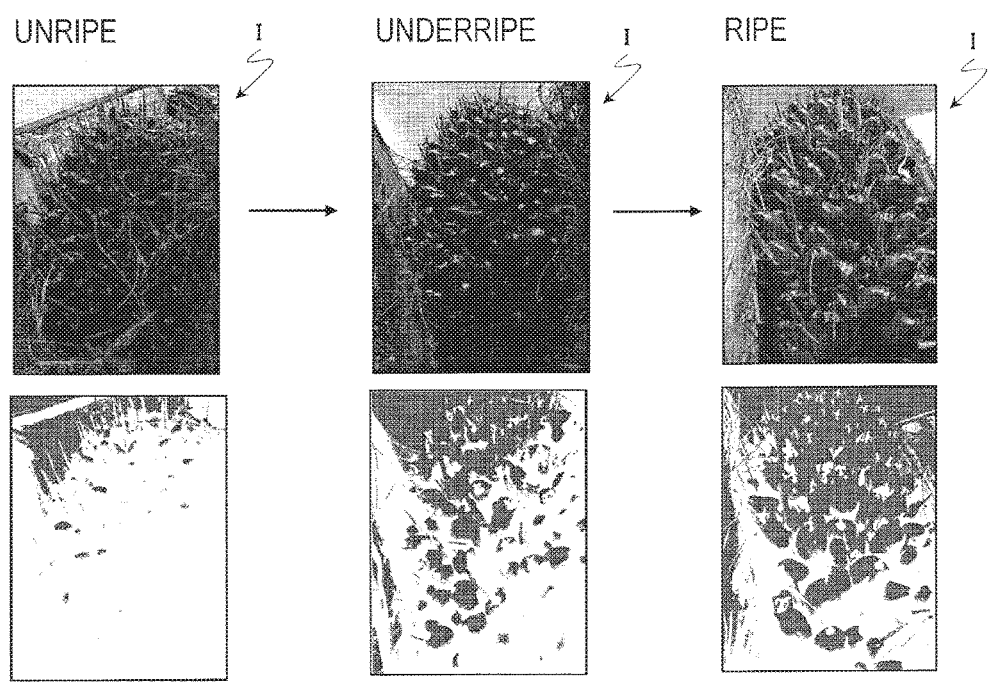
FIG. 8 shows images I acquired by image capturing of the entirety of the bunches F of three maturity levels (unripe, underripe, and ripe), and pixel distributions, at the respective maturity levels, of pixels having a pixel value larger than, or equal to, a reference value among the pixels that have a pixel value NIRS and are included in the images I.

FIG. 8 shows the images I acquired by image capturing of the entirety of the bunches F of three maturity levels (unripe, underripe and ripe), and also shows, for each maturity level, the distribution of the pixels having a pixel value higher than, or equal to, a reference value, among the pixels having the pixel value NIRS included in the pixel I. In this embodiment, the pixel value is represented by, for example, the 8-bit system (values of 0 to 255). The reference value may be, for example, "80". In this specification, the pixel value may be referred to also as the "gray scale value".

It is now assumed that all the pixel values in the image I including the entirety of the bunch F are simply averaged. The average value may vary by an influence of the background, the shadow between the fruits or the like, which may be included in the image I. With the determination method in this embodiment, the area size ratio of the intensity distribution of the near infrared light is found on the basis of the predetermined reference value and in consideration of the intensity distribution of the blue light. FIG. 8 shows, for each maturity level, how the pixels having a pixel value of, for example, 80 or larger, among the pixels having the pixel value NIRS included in the image I, are distributed in the image I. As the maturity level of the bunch F rises, the density of the pixels (pixel distribution) increases. This indicates that the maturity determination information may be obtained based on the pixel distribution on the basis of the reference value. It should be noted that the pixel distribution still includes information on the background or the like.

Portion (a) of FIG. 9A shows an image including the entirety of the bunch F that is unripe. Portion (b) of FIG. 9A shows, in an enlarged manner, the rectangular part of the image shown in portion (a) of FIG. 9A represented by the dashed line. Portion (c) of FIG. 9A shows a mapping image obtained as a result of the pixel distribution of pixels in a range of predetermined pixel values being mapped based on the pixel value NIRS in the image I shown in portion (b) of FIG. 9A. Portion (d) of FIG. 9A shows a mapping image obtained as a result of the pixel distribution of pixels in the range of predetermined pixel values being mapped based on a quotient value obtained by dividing the pixel value NIRS in the image I shown in portion (b) of FIG. 9A by the pixel value BLUS.

Portion (a) of FIG. 9B shows an image including the entirety of the bunch F that is underripe. Portion (b) of FIG. 9B shows, in an enlarged manner, the rectangular part of the image shown in portion (a) of FIG. 9B represented by the dashed line. Portion (c) of FIG. 9B shows a mapping image obtained as a result of the pixel distribution of pixels in the range of predetermined pixel values being mapped based on the pixel value NIRS of the plurality of first pixels included in the image I shown in portion (b) of FIG. 9B. Portion (d) of FIG. 9B shows a mapping image obtained as a result of the pixel distribution of pixels in the range of predetermined pixel values being mapped based on a quotient value obtained by dividing the pixel value NIRS in the image I shown in portion (b) of FIG. 9B by the pixel value BLUS.

Portion (a) of FIG. 9C shows an image including the entirety of the bunch F that is ripe. Portion (b) of FIG. 9C shows, in an enlarged manner, the rectangular part of the image shown in portion (a) of FIG. 9C represented by the dashed line. Portion (c) of FIG. 9C shows a mapping image obtained as a result of the pixel distribution of pixels in the range of predetermined pixel values being mapped based on the pixel value NIRS of the plurality of first pixels included in the image I shown in Portion (b) of FIG. 9C. Portion (d) of FIG. 9C shows a mapping image obtained as a result of the pixel distribution of pixels in the range of predetermined pixel values being mapped based on a quotient value obtained by dividing the pixel value NIRS in the image I shown in portion (b) of FIG. 9C by the pixel value BLUS. The "division of the pixel values" refers to dividing the pixel value of a pixel by the pixel value of another pixel associated with the above-mentioned pixel in the pixel unit.

For example, it is now assumed that the entirety of the bunch F is processed with image capturing from far to acquire the image I shown in portion (a) of FIG. 9A. In this case, as described above, the image I includes complicated information other than the bunch F, for example, the background, the shadow and the like. Such complicated information may possibly have adverse information on the maturity determination. In order to suppress this influence, it is preferable to perform image capturing of, for example, the rectangular part represented by the dashed line shown in portion (a) of FIG. 9A in an enlarged manner. As a result, the image I shown in portion (b) of FIG. 9A is acquired. In this case, the image capturing device 200 may include a narrow angle lens having a relatively long focal distance, or may include an optical zoom lens. Alternatively, the image capturing device 200 may have an electronic zoom function, needless to say. The rectangular part preferably includes at least three fruits.

After an image including one or a plurality of bunches F or the entirety of the oil palm tree is acquired by the image capturing device 200, the calculation device P may extract the rectangular part represented by the dashed line from such an image by trimming. In other words, the calculation device P may use a trimming function to acquire the image I shown in portion (b) of FIG. 9A. In this manner, in the case where, for example, an image of the entirety of the oil palm tree is captured from far, information on the fruits necessary for the maturity determination may be preferably obtained while the above-described complicated information is eliminated. It is preferable that the image I to be trimmed also includes at least three fruits.

For performing image capturing of the bunch F or the entirety of the oil palm tree, a part of bunch F including, for example, three fruits may be automatically specified (recognized) by image recognition. Trimming may be performed in substantially the same manner. An example of usable image recognition technology may be any of a wide range of known pattern recognition technologies. It may be analyzed which of patterns corresponding to a classification prepared in advance (fruit, branch, leaf, etc.) matches the subject, so as to determine which class the subject is. Pattern recognition is performed by use of, for example, a trainable pattern recognition system using mathematical, geometrical and harmonic-shape descriptors. Such a system is educated so as to select a possible class by use of a knowledge base learned by contacting a large number of samples of the classification prepared in advance. A training set includes thousands of basic types of images for each class. Successful pattern matching is caused when an untrained descriptor on the target matches a trained descriptor on the target. The above-described pattern recognition system is described in detail in, for example, Japanese Laid-Open Patent Publication No. 2015-046162.

The mapping image shown in portion (c) of FIG. 9A is generated based on the pixel value NIRS included in the image I, and includes mapping images of the three hierarchical layers I, II and III. For example, the mapping image of the hierarchical layer I includes a distribution of pixels having a gray scale value of 60 or larger and smaller than 70 among the gray scale values of 0 to 255. The mapping image of the hierarchical layer II includes a distribution of pixels having a gray scale value of 70 or larger and smaller than 80 among the gray scale values of 0 to 255. The mapping image of the hierarchical layer III includes a distribution of pixels having a gray scale value of 80 or larger among the gray scale values of 0 to 255. The mapping images shown in portions (c) of FIG. 9B and FIG. 9C each include mapping images of the three hierarchical layers I, II and III described above.

The mapping image shown in portion (d) of FIG. 9A is generated based on a quotient value obtained by dividing the pixel value NIRS included in the image I by the pixel value BLUS, and includes mapping images of the three hierarchical layers I, II and III. For example, the mapping image of the hierarchical layer I includes a distribution of pixels having a gray scale value of 60 or larger and smaller than 70 among the gray scale values of 0 to 255. The mapping image of the hierarchical layer II includes a distribution of pixels having a gray scale value of 70 or larger and smaller than 80 among the gray scale values of 0 to 255. The mapping image of the hierarchical layer III includes a distribution of pixels having a gray scale value of 80 or larger. The mapping images shown in portions (d) of FIG. 9B and FIG. 9C each include mapping images of the three hierarchical layers I, II and III described above.

The calculation device P, for example, maps the pixel distribution with blue to generate a blue mapping image of hierarchical layer I, maps the pixel distribution with green to generate a green mapping image of hierarchical layer II, and maps the pixel distribution with red to generate a red mapping image of hierarchical layer III. The calculation device P places the mapping images of the three hierarchical layers I, II and III such that the images overlap each other to generate the mapping image. However, the calculation device P does not need to generate all the color mapping images of the three hierarchical layers I, II and III. The calculation device P merely needs to generate at least a color mapping image of the hierarchical layer III based on one threshold value (e.g., "80"). The number of the hierarchical layers may be determined in accordance with, for example, the number of maturity levels.

In this embodiment, the calculation device P generates the mapping image shown in portion (d) of FIG. 9A on the unripe bunch F. The calculation device P also generates the mapping image shown in portion (d) of FIG. 9B on the underripe bunch F and the mapping image shown in portion (d) of FIG. 9C on the ripe bunch F. The calculation device P may determine the maturity level by use of these mapping images.

As can be seen from the mapping images shown in portions (c) of FIG. 9A, FIG. 9B and FIG. 9C, as the maturity level of the bunch F rises, the intensity of the reflected light of the near infrared light, namely, the value of the pixel value NIRS increases. As a result, the density of the pixels of the hierarchical layer III is raised. However, the pixel distributions in the mapping images on the underripe bunch F and the ripe bunch F do not appear to be much different from each other because of the influence of the near infrared light in the external disturbing light (mainly, sunlight).

As described above, the reflectance of the blue light does not vary almost at all in accordance with the maturity level, and therefore, is usable as intensity reference for the reflected light for suppressing the influence of the sunlight. In the mapping images shown in portions (d) of FIG. 9A, FIG. 9B and FIG. 9C, a sufficient difference is easily seen between the pixel distributions on the mapping images on the underripe bunch F and the ripe bunch F. A reason for this is that these mapping images are obtained based on a quotient value obtained by dividing the pixel value NIRS in the image I by the pixel value BLUS, and thus the influence of the sunlight is suppressed. This indicates that the maturity level of the bunch F is determinable with high precision by appropriately setting the threshold value for the gray scale value for a mapping image generated based on the quotient value.

Now, it will be discussed on generating a mapping image based on a difference value obtained by subtracting the pixel value BLUS in the image I from the pixel value NIRS. In this case, it is not possible to determine, with high precision, the maturity level of the bunch F with the influence of the sunlight being suppressed. It is known that, for example, the spectrum of the sunlight significantly varies between in a sunlit area and in a shadow area or between on a cloudy day and on a day of good weather. It is known that the intensity of light of a visible wavelength band on a cloudy day is about ⅓ of that of a day of good weather, whereas the intensity of the near infrared light is not different almost at all. On a day of good weather and also on a cloudy day, the intensity of the blue light is several times as high as the intensity of the near infrared light. In other words, the intensity of the blue light incident on the bunch F is several times as high as the intensity of the near infrared light incident on the bunch F. By contrast, the intensity of the near infrared light reflected by the bunch F is several times as high as the intensity of the blue light reflected by the bunch F.

At least in a sunlit area, the intensity of the blue light included in the external disturbing light is high. Therefore, in the case where the pixel value BLUS included in the image I is subtracted from the pixel value NIRS, a difference in accordance with the maturity level is not seen in the difference value, namely, the post-subtraction signal. By contrast, in this embodiment, the pixel value NIRS included in the image I is divided by the pixel value BLUS. In this case, even though the intensity of the blue light included in the external disturbing light is high, the post-division signal still includes a signal component representing information in accordance with the maturity level. Such a signal component is, for example, amplified by the signal processing.

Figure 10:
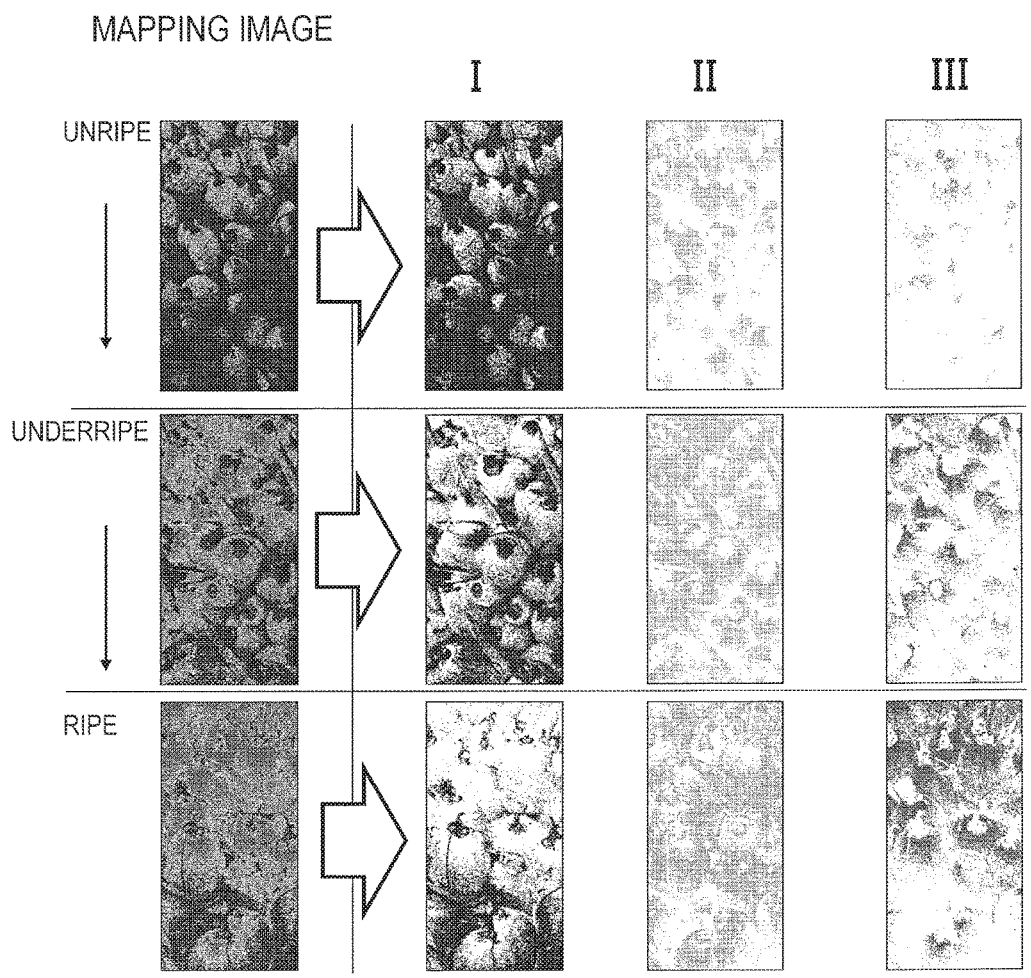
FIG. 10 shows color mapping images obtained as a result of dividing each of three mapping images on the unripe, underripe and ripe bunches F into three hierarchical layers I, II and III.

Referring to FIG. 10, the three mapping images on the unripe, underripe and ripe bunch F shown in portions (d) of FIG. 9A, FIG. 9B and FIG. 9C are each divided into the three hierarchical layers I, II and III. FIG. 10 shows the color mapping images of the respective hierarchical layers. As shown in FIG. 10, regarding the color mapping images of the hierarchical layer I, the density of the pixels (pixel distribution) is highest in the color mapping image on the unripe bunch F and lowest in the color mapping image on the ripe bunch F. Regarding the color mapping images of the hierarchical layer II, the density of the pixels is highest in the color mapping image on the underripe bunch F and lowest in the color mapping image on the unripe bunch F. Regarding the color mapping images of the hierarchical layer III, the density of the pixels is highest in the color mapping image on the ripe bunch F and lowest in the color mapping image on the unripe bunch F.

The pixel distribution corresponds to the area size ratio AR of the intensity distribution of the near infrared light obtained on the basis of the predetermined reference value and in consideration of the intensity distribution of the blue light for each hierarchical layer. Specifically, the area size ratio AR is the ratio of the number of pixels having a quotient value fulfilling a condition for the reference value among pixels as targets of division, with respect to the number of the plurality of first pixels. For example, the pixel unit shown in FIG. 2 is subjected to division computation on a pixel-by-pixel basis by use of the pixel values of the pixel 221C and the pixel 221D that are associated with each other. The number of the pixels that are the targets of division typically matches the number of the plurality of first pixels. For example, in the case where one pixel unit includes three pixels 221C including the IR filter and one pixel 221D including the B filter, the pixel value NIRS of each of the three pixels 221C may be divided by the pixel value BLUS of the pixel 221D.

For example, the lower limit of the reference value (lower-limit threshold value) and the upper limit of the reference value (upper-limit threshold value) used for the hierarchical layer I are respectively 60 and 70. The lower limit and the upper limit of the reference value used for the hierarchical layer II are respectively 70 and 80. The lower limit of the reference value used for the hierarchical layer III is 80. The upper limit is not set. An appropriate reference value may be set, so that the maturity level of the bunch F is determined based on the density of the pixels, namely, the area size ratio AR.

Figure 11:
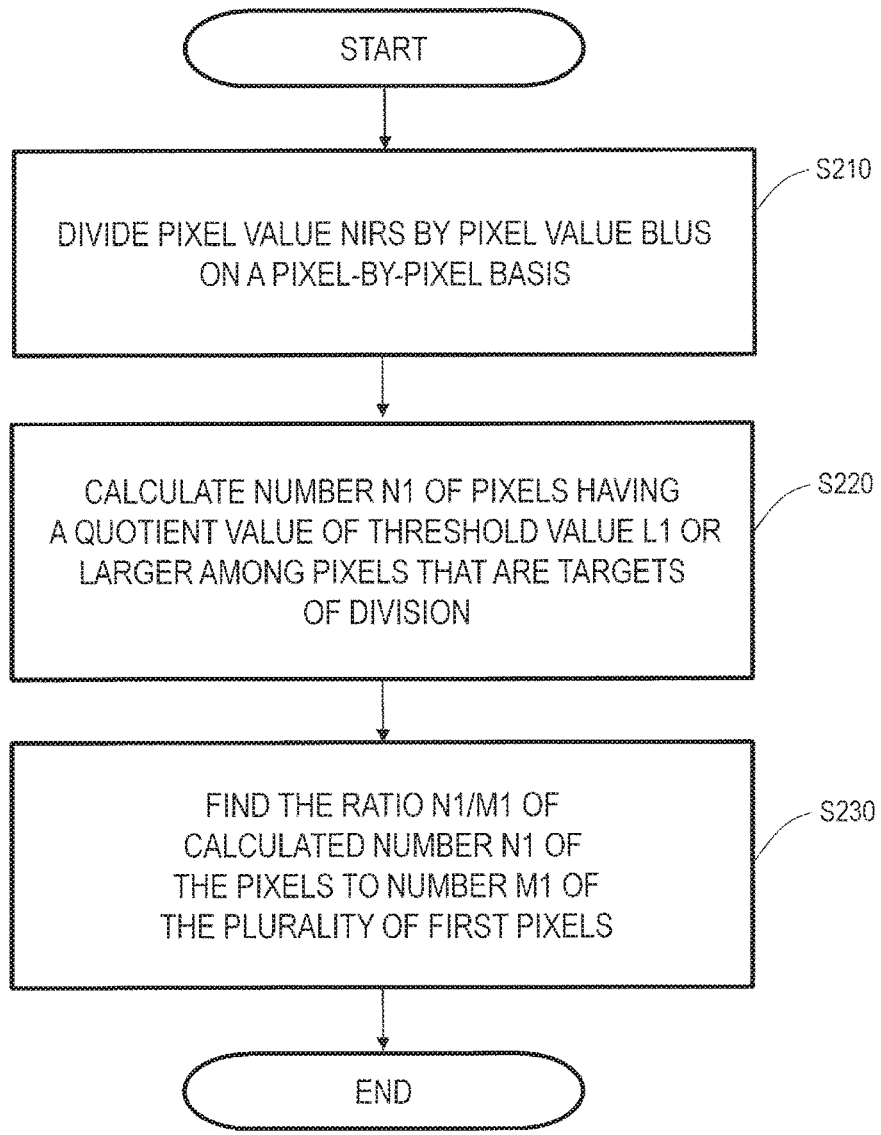
FIG. 11 is a flowchart showing a specific processing procedure in step S200 in embodiment 1 in detail.

FIG. 11 shows a specific processing procedure in step S200 this embodiment in detail. The calculation device P finds the area size ratio AR of the intensity distribution of the near infrared light on the basis of the predetermined reference value and in consideration of the intensity distribution of the blue light. Specifically, in step S210, the calculation device P divides the pixel values NIRS obtained from the plurality of first pixels included in the image I by the pixel values BLUS obtained from the plurality of second pixels associated with the plurality of first pixels.

The influence of the sunlight on the maturity determination may keep on varying at each determination (i.e., at each image capturing operation). Therefore, a standard white plate is conventionally necessary in order to remove the influence. In this embodiment, the pixel value NIRS is divided by the pixel value BLUS. As a result, the influence of the sunlight is suppressed and thus the standard white plate is not necessary. This simplifies the maturity determination process.

The spectral characteristics of the standard white plate are different from the spectral characteristics of the light reflected by the bunch F. Therefore, in the case where the influence of the sunlight is removed by use of the standard white plate, the maturity determination result may include the difference between the spectral characteristics of the standard white plate and the spectral characteristics of the reflected light as a determination error. In this embodiment, the standard white plate is not used, but the pixel value NIRS is divided by the pixel value BLUS. Therefore, the maturity level is determined with high precision.

In step S220, the calculation device P calculates the number N1 of pixels having a quotient value larger than, or equal to, a threshold value L1 among the pixels that are the targets of division. The number of the pixels that are the targets of division typically matches the number M1 of the plurality of first pixels. For example, for the hierarchical layer III shown in FIG. 10, "80" may be set as the threshold value L1. As a result of computation, the number of pixels having a pixel value (i.e., quotient value) of "80" or larger is N1. Alternatively, N1 may be the number of pixels having a quotient value smaller than, or equal to, the threshold value L1, and in step S220, the calculation device P may calculate the number N1 among the pixels that are the targets of division.

In step S230, the calculation device P finds the ratio N1/M1, namely, the ratio the calculated number N1 of the pixels with respect to the number M1 of the plurality of first pixels (or the number of the pixels that are the targets of division). The calculation device P may generate a color mapping image in correspondence with each of the hierarchical layers based on the ratio N1/M1.

Now, FIG. 6 is referred to again.

(Step S300)

The calculation device P generates maturity determination information in accordance with the area size ratio AR. Specifically, the calculation device P generates the maturity determination information in accordance with a result of comparing the ratio N1/M1 against a threshold value R1.

Figure 12A:
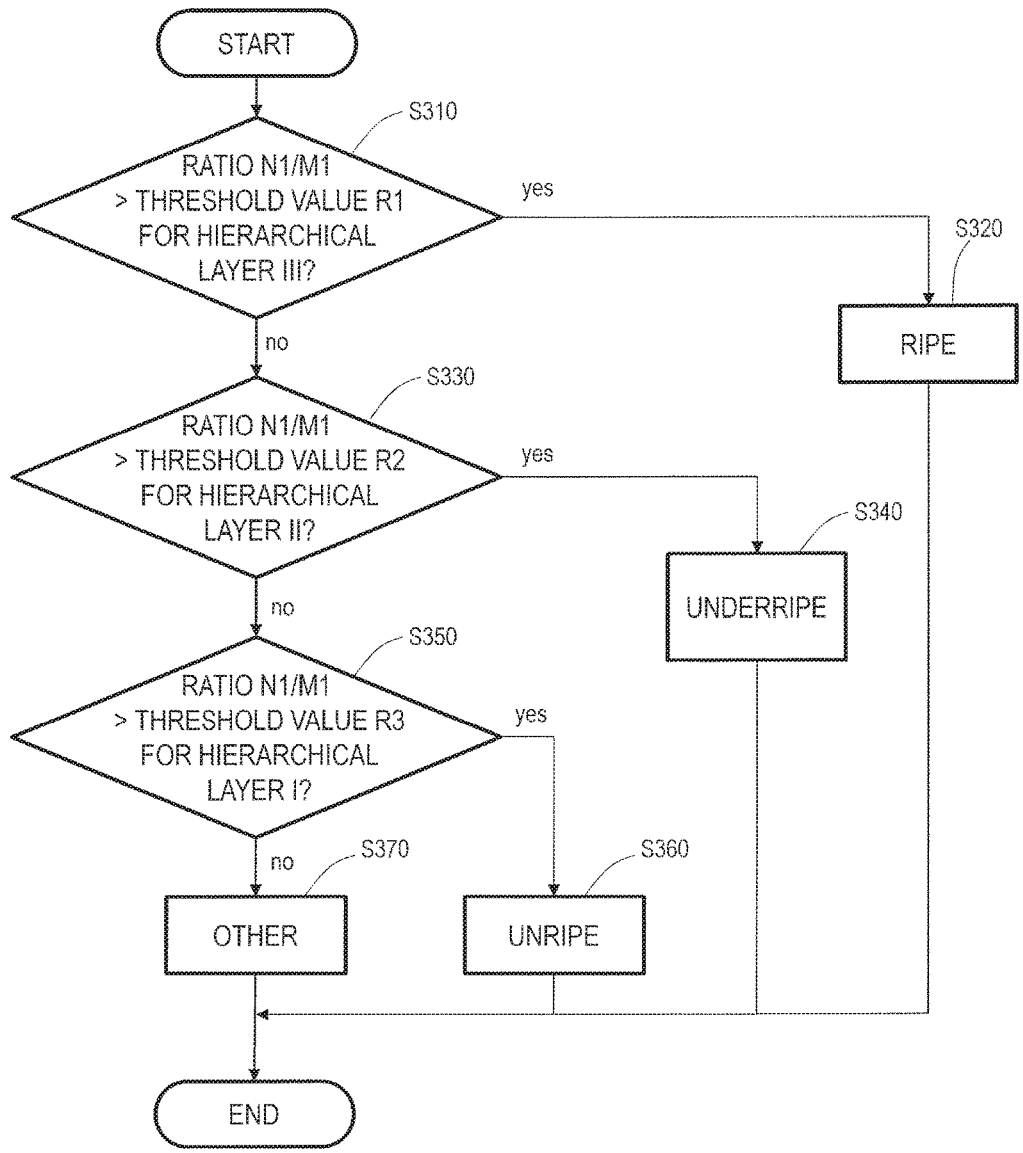
FIG. 12A is a flowchart showing a specific processing procedure in step S300 in embodiment 1 in detail.

FIG. 12A shows a specific processing procedure in step S300 in detail. First, a procedure of determining whether the maturity level of the bunch F is "ripe" or not will be described. In step S310, the calculation device P determines whether the ratio N1/M1 calculated for the hierarchical layer III is larger than the threshold value R1 or not. The threshold value R1 is appropriately determined by the designing specifications or the like, and is, for example, stored in advance in an internal ROM (not shown) of the calculation device P. All the threshold values described in this specification, including the threshold value R1, are stored in the internal ROM. In the case where the ratio N1/M1 is larger than the threshold value R1, in step S320, the calculation device P generates maturity determination information representing "ripe". In the case where the ratio N1/M1 is smaller than, or equal to, the threshold value R1, the calculation device P generates maturity determination information representing, for example, "not ripe". The maturity determination information may be represented by, for example, a 1-bit signal, where "0" may be assigned to "not ripe" and "1" may be assigned to "ripe". With the above-described procedure, the maturity determination information representing whether the maturity level of the bunch F is "ripe" or not is obtained.

For example, it may be further determined whether the maturity level is "underripe" or "unripe". Referring to FIG. 12A, in the case where the ratio N1/M1 is determined to be smaller than, or equal to, the threshold value R1 in step S310, it is at least known that the maturity level is not "ripe". In step S330, the calculation device P finds the ratio N1/M1 for the hierarchical layer II and compares the ratio against a threshold value R2.

Specifically, for the hierarchical layer II, the calculation device P calculates, among the pixels that are the targets of division, the number N1 of pixels having a quotient value larger than, or equal to, the lower limit of a threshold value L2 and smaller than the upper limit of the threshold value L2. As described above, for example, the lower limit of the threshold value L2 may be set to "70" and the upper limit of the threshold value L2 may be set to "80". Like in step S230, for the hierarchical layer II, the calculation device P finds the ratio N1/M1, namely, the ratio the calculated number N1 of the pixels with respect to the number M1 of the plurality of first pixels.

In step S330, the calculation device P determines whether the ratio N1/M1 calculated for the hierarchical layer II is larger than the threshold value R2 or not. In the case where the ratio N1/M1 is larger than the threshold value R2, the calculation device P generates maturity determination information representing "underripe" in step S340. In the case where the ratio N1/M1 is smaller than, or equal to, the threshold value R2, the procedure goes to step S350.

In step 350, the calculation device P finds the ratio N1/M1 for the hierarchical layer I and compares the ratio against a threshold value R3. Specifically, for the hierarchical layer I, the calculation device P calculates, among the pixels that are the targets of division, the number N1 of pixels having a quotient value larger than, or equal to, the lower limit of a threshold value L3 and smaller than the upper limit of the threshold value L3. As described above, for example, the lower limit of the threshold value L3 may be set to "60" and the upper limit of the threshold value L3 may be set to "70". Like in step S230, for the hierarchical layer I, the calculation device P finds the ratio N1/M1, namely, the ratio the calculated number N1 of the pixels with respect to the number M1 of the plurality of first pixels.

In step S350, the calculation device P determines whether the ratio N1/M1 calculated for the hierarchical layer I is larger than the threshold value R3 or not. In the case where the ratio N1/M1 is larger than the threshold value R3, the calculation device P generates maturity determination information representing "unripe" in step S360. In the case where the ratio N1/M1 is smaller than, or equal to, the threshold value R3, the calculation device P generates maturity information representing, for example, "other" in step S370. The maturity determination information may be represented by, for example, a 2-bit signal, where "11" may be assigned to "ripe", "10" may be assigned to "underripe", "01" may be assigned to "unripe", and "00" may be assigned to "other". In this manner, the maturity determination information representing "underripe" or "unripe" may be generated in addition to the maturity determination information representing "ripe".

Figure 12B:
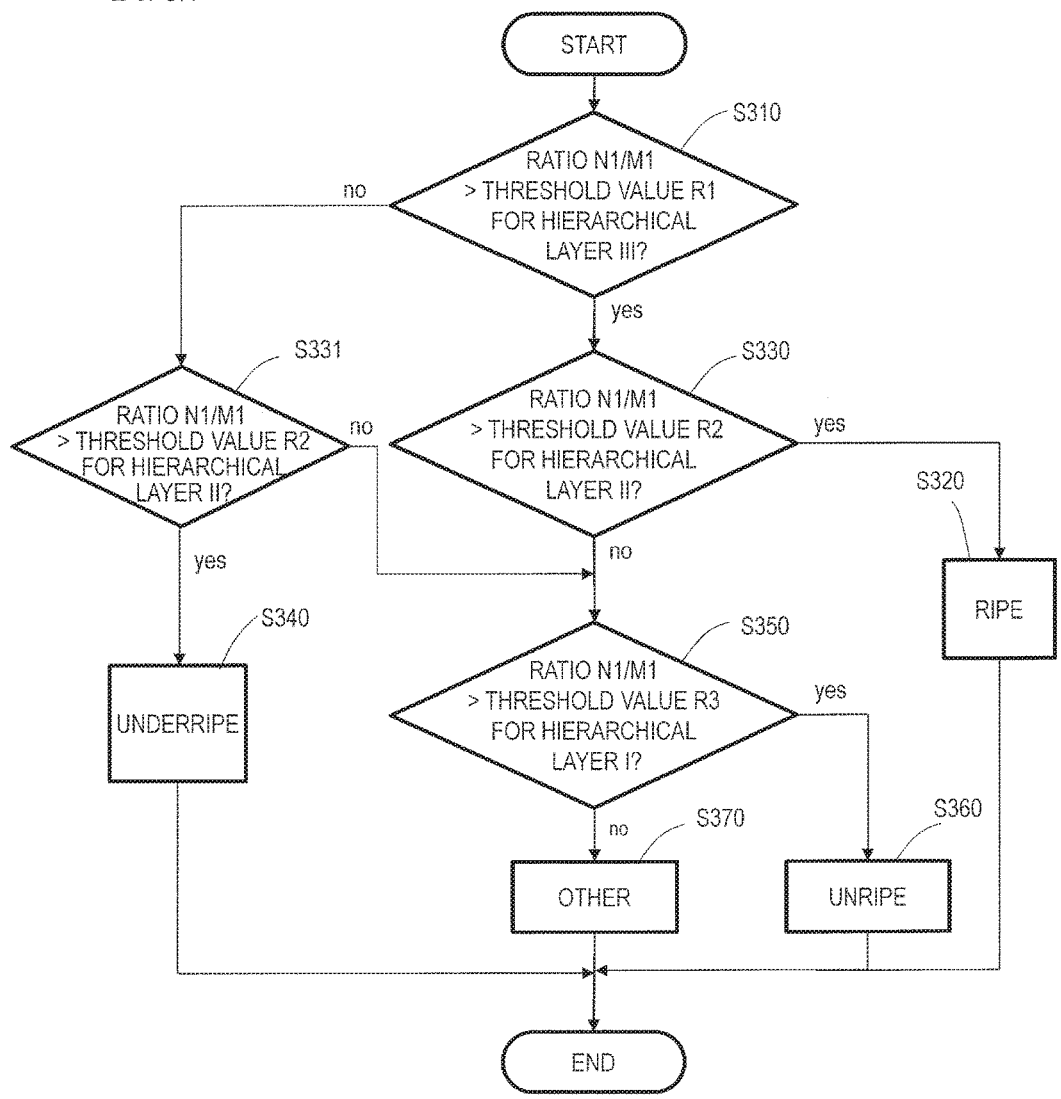
FIG. 12B is a flowchart showing another specific processing procedure in step S300 in embodiment 1 in detail.

FIG. 12B shows another specific processing procedure in step S300 in detail. As shown in FIG. 12B, in the case where the ratio N1/M1 is larger than the threshold value R1 for the hierarchical layer III and the ratio N1/M1 is larger than the threshold value R2 for the hierarchical layer II, the calculation device P can generate maturity determination information representing "ripe". In this manner, the maturity determination information can be generated using a plurality of hierarchical layers.

Now, FIG. 6 is referred to again.

(Step S400)

In accordance with the maturity determination information, the calculation device P generates a driving signal for driving the notification device 500 notifying, for example, the farmer of the maturity level of the bunch F. For example, the notification device 500 may include an LED. In such a structure, in the case where the maturity determination information represents "ripe", the calculation device P generates a driving signal for causing the LED to emit light (signal for turning on the LED). In the case where the maturity determination information represents "not ripe", the calculation device P does not generate a driving signal for causing the LED to emit light. The notification device 500 may include a plurality of LEDs emitting light of different colors. In the case where the maturity determination information includes various maturity levels (e.g., "ripe", "underripe" and "unripe"), the calculation device P, for example, may generate a driving signal for causing any one of the plurality of LEDs to emit light in accordance with the maturity level. In this manner, the farmer recognizes the maturity level of the bunch F in accordance with the color of the light emitted by the LED.

For example, the notification device 500 may include a speaker. In such a structure, in the case where the maturity determination information represents "ripe", the calculation device P generates a driving signal for causing the speaker to output a sound (signal for turning on the speaker). In the case where the maturity determination information represents "not ripe", the calculation device P does not generate a driving signal for causing the speaker to output a sound. In the case where the maturity determination information includes various maturity levels, the calculation device P, for example, may drive the speaker such that the loudness of the sound is changed in accordance with the maturity level.

For example, the notification device 500 may include a vibrator. In such a structure, in the case where the maturity determination information represents "ripe", the calculation device P generates a driving signal for causing the vibrator to vibrate (signal for turning on the vibrator). In the case where the maturity determination information represents "not ripe", the calculation device P does not generate a driving signal for causing the vibrator to vibrate. In the case where the maturity determination information includes various maturity levels, the calculation device P, for example, may drive the vibrator such that the strong/weak pattern of the vibration is changed in accordance with the maturity level.

For example, the notification device 500 may include a liquid crystal display. In such a structure, in the case where the maturity determination information represents "ripe", the calculation device P generates a driving signal for causing the liquid crystal display to display letter information "ripe". In the case where the maturity determination information represents "not ripe", the calculation device P generates a driving signal for causing the liquid crystal display to display letter information "not ripe". For example, the liquid crystal display may display a symbol such as "○", "X" or the like instead of the letter information, or may change the color of display in accordance with the maturity level.

The calculation device P may generate a color image of the bunch F based on the pixel values REDS, GLNS and BLUS obtained from the RGB pixels of the image sensor 220. The calculation device P may generate a maturity level image including information on the reference value and representing the maturity level, based on the maturity determination information. The maturity level image is, for example, the mapping image shown in portion (d) of FIG. 9A. The calculation device P may display the maturity level image, as overlapping the color image, on the liquid crystal display. In this case, the calculation device P may also display information on the threshold value used for the computation on the liquid crystal display. In this case, the farmer easily checks the actual position in the color image in relation with the mapping image. Thus, the harvest efficiency is improved.

The calculation device P may also determine whether the bunch F is harvestable or not based on the maturity determination information. For example, it is now assumed that there are four maturity levels of "ripe", "slightly ripe", "underripe" and "unripe". In the case where, for example, the maturity determination information represents "ripe" or "slightly ripe", the calculation device P determines that the bunch F is harvestable. In the case where the maturity determination information represents "underripe" or "unripe", the calculation device P determines that the bunch F is not harvestable. For example, the liquid crystal display may display letter information representing whether the bunch F is harvestable or not in accordance with the determination information. With such display, the information on whether the bunch F is harvestable or not is transmitted to the farmer directly, which supports the farmer more.

The calculation device P may output the maturity determination information to outside via, for example, an output IF (not shown) instead of performing the operation in step S400. In the case where, for example, the notification device 500 has a function of generating a signal for driving the notification device 500 itself, the notification device 500 may receive the maturity determination information from the calculation device P and generate a driving signal in accordance with the maturity determination information.

In this embodiment, the variance in the determination on the maturity level at the time of harvest of oil palm is made smaller, regardless whether the farmer is experienced or not, than by a conventional method by which the maturity level is determined by visual observation. In addition, the pixel value NIRS is divided by the pixel value BLUS, and thus the maturity level is determined with high precision with the influence of the sunlight being suppressed, with no use of the standard white plate. The time to harvest the oil palm is determined with high precision without decreasing the efficiency of the harvesting work. Therefore, it is expected that the production amount of the oil component contained in the oil palm is increased.

Embodiment 2

According to a determination method in this embodiment, the calculation device P receives an image I including the intensity distributions of the light in the first, second and third wavelength bands in step S100, and generate maturity determination information based on the intensity distributions of light in the first, second and third wavelength bands in step S300. In other words, the calculation device P generates the maturity determination information based on the pixel values NIRS, BLUS and REDS obtained from the plurality of first, second and third pixels. The intensity of light of the third wavelength band that is reflected by the bunch F varies in accordance with the maturity level. The third wavelength band is different from the first wavelength band (i.e., the wavelength band of the near infrared light). The third wavelength band is a wavelength band of, for example, red light, which is visible light.

Figure 13:
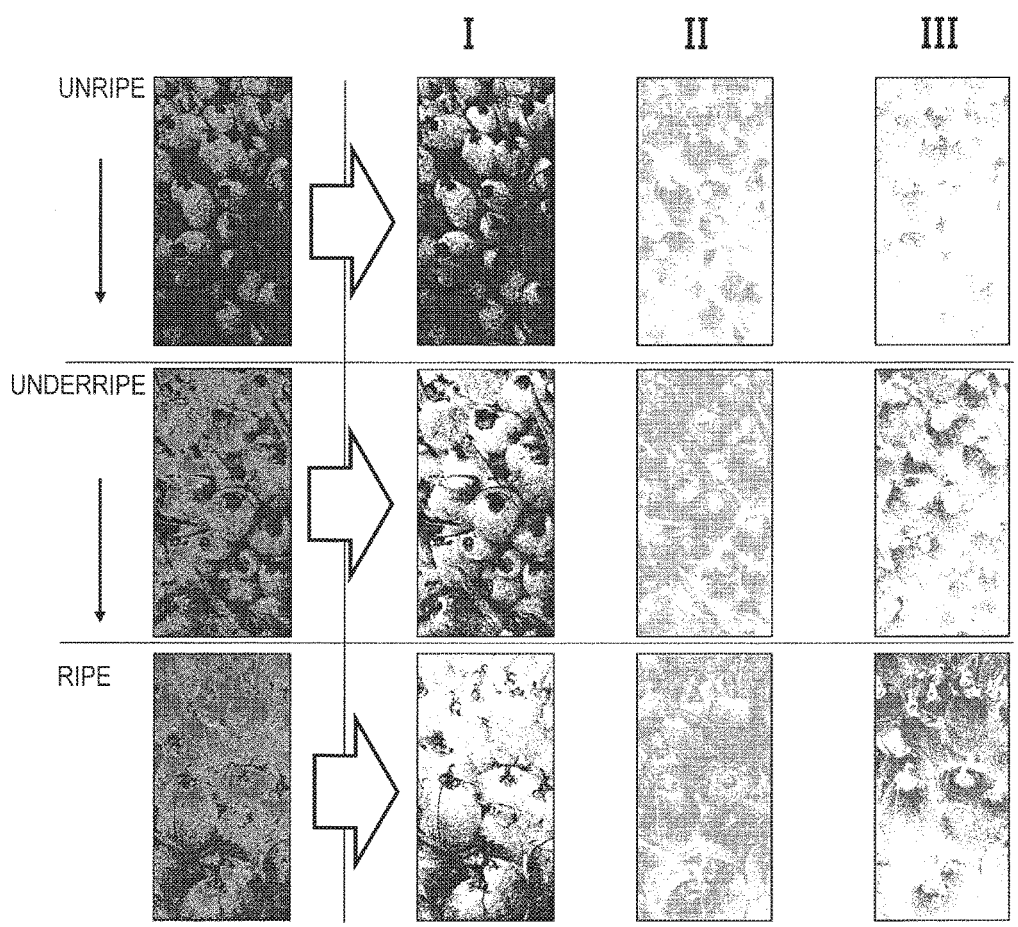
FIG. 13 shows color mapping images obtained as a result of dividing each of three mapping images on the unripe, underripe and ripe bunches F into the three hierarchical layers I, II and III.

FIG. 13 shows color mapping images obtained as a result of dividing each of three mapping images on the unripe, underripe and ripe bunches F into the three hierarchical layers I, II and III, like FIG. 10. The unripe, underripe and ripe bunches F used for maturity determination are the rectangular parts shown in portions (a) of FIG. 9A, FIG. 9B and FIG. 9C. The mapping images shown in FIG. 13 are generated based on a quotient value obtained by dividing the sum value, of the pixel value NIRS and the pixel value REDS in the image I, by the pixel value BLUS. The "addition of the pixel values" refers to adding pixel values of pixels associated with each other in the pixel unit.

As shown in FIG. 13, regarding the color mapping images of the hierarchical layer I, the density of the pixels (pixel distribution) is highest in the color mapping image on the unripe bunch F and lowest in the color mapping image on the ripe bunch F. Regarding the color mapping images of the hierarchical layer II, the density of the pixels is highest in the color mapping image on the underripe bunch F and lowest in the color mapping image on the unripe bunch F. Regarding the color mapping images of the hierarchical layer III, the density of the pixels is highest in the color mapping image on the ripe bunch F and lowest in the color mapping image on the unripe bunch F.

Figure 14:
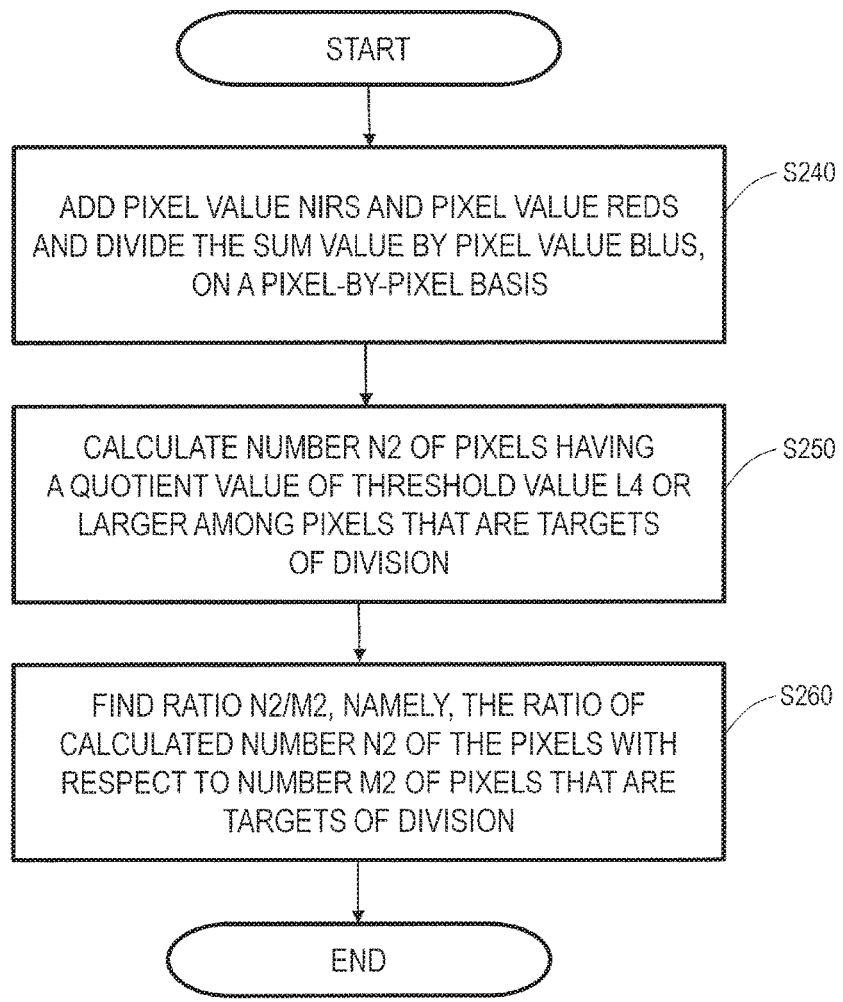
FIG. 14 is a flowchart showing a specific processing procedure in step S200 in embodiment 2 in detail.

FIG. 14 shows a specific processing procedure in step S200 in detail in this embodiment. In step S240, the calculation device P divides, on a pixel-by-pixel basis, the sum value, obtained by adding the pixel values NIRS obtained from the plurality of first pixels and the pixel values REDS obtained from the plurality of third pixels on a pixel-by-pixel basis, by the pixel values BLUS obtained from the plurality of second pixels. For example, regarding the pixel unit including the pixels 221 in two rows by two columns shown FIG. 2, the calculation device P adds the pixel value NIRS obtained from the pixel 221C and the pixel value REDS obtained from the pixel 221A. The calculation device P divides the resultant sum value by the pixel value BLUS obtained from the pixel 221D.

In step S250, the calculation device P calculates the number N2 of pixels having a quotient value larger than, or equal to, the threshold value L4 among the pixels that are the targets of division. Typically, the number M2 of the pixels that are the targets of addition/division matches the number of the plurality of first pixels. For example, it is assumed that one pixel unit includes two pixels 221C including the IR filter, one pixel 221D including the B filter and one pixel 221A including the R filter. In this case, the pixel value NIRS of each of the two pixels 221C may be added with the pixel value REDS of the pixel 221A, and then the resultant sum value may be divided by the pixel value BLUS of the pixel 221D. Alternatively, N2 may be the number of pixels having a quotient value smaller than, or equal to, the threshold value L4, and in step S250, the calculation device P may calculate the number N2 among the pixels that are the targets of division.

In step S260, the calculation device P finds the ratio N2/M2, namely, the ratio of the calculated number N2 of the pixels with respect to the number M2 of the pixels that are the targets of division.

The pixel distribution is represented by the ratio N2/M2, and corresponds to the area size ratio AR, for each hierarchical layer, of the sum of the intensity distributions of the near infrared light and the red light obtained on the basis of the predetermined reference value and in consideration of the intensity distribution of the blue light. For example, the lower limit of the reference value (lower-limit threshold value) and the upper limit of the reference value (upper-limit threshold value) used for the hierarchical layer I are respectively 90 and 100. The lower limit and the upper limit of the reference value used for the hierarchical layer II are respectively 100 and 110. The lower limit of the reference value used for the hierarchical layer III is 110. The upper limit is not set.

Next, the calculation device P follows the processing procedure shown in, for example, FIG. 12A to generate the maturity determination information in accordance with a result of comparing the ratio N2/M2 against a threshold value R4 for each hierarchical layer. Specifically, like in step S310, the calculation device P determines which of the ratio N2/M2 for the hierarchical layer III and the threshold value R4 is larger or smaller. In the case where the ratio N2/M2 is larger than threshold value R4, the calculation device P generates maturity determination information representing "ripe" like in step S320.

In this embodiment, the sum value of the pixel value NIRS and the pixel value REDS is divided by the pixel value BLUS, so that the precision of the maturity determination is further improved.

Embodiment 3

According to a determination method in this embodiment, unlike the determination method in embodiment 2, maturity determination information is generated based on a difference value obtained by subtracting the pixel value REDS from the pixel NIRS. The "subtraction of the pixel values" refers to subtracting the pixel value of a pixel from the pixel value of another pixel associated with the above-mentioned pixel in the pixel unit.

For example, the light reflected by the bunch F includes light reflected by the fruits and also light reflected by the dead calyx and leaves covering the fruits. The dead calyx and leaves contains little chlorophyll, which is a main component of chloroplast. Therefore, the reflectance characteristic of the light reflected by the dead calyx and leaves is generally uniform in a wavelength band from the red light to the near infrared light. By contrast, as shown in FIG. 7, the light reflected by the bunch F has a reflectance characteristic that the reflectance is especially high in a part of the wavelength from the red light to the near infrared light. The image I acquired by the image capturing device 200 may include the dead calyx and leaves. Therefore, the image I used for the determination method in each of embodiments 1 and 2 may include complicated information caused by the dead calyx and leaves. In this embodiment, the above-described difference between the reflectance characteristic of the light reflected by the dead calyx and leaves and the reflectance characteristic of the light reflected by the fruits is paid attention to, and a difference between an image A formed of the pixel value NIRS and an image B formed of the pixel value REDS is found. The image A includes the dead calyx and leaves, and the image B mainly includes the dead calyx and leaves. The difference between the image A and the image B is found, so that information mainly caused by the fruits is selectively obtained.

With the determination method in this embodiment, in step S100, the calculation device P receives the image I including the intensity distributions of light of the first, second and third wavelength bands. In step S300, the calculation device P generates the maturity determination information based on the intensity distributions of light of the first, second and third wavelength bands. In other words, the calculation device P generates the maturity determination information based on the pixel values NIRS, REDS and BLUS obtained from the plurality of first, second and third pixels.

Figure 15:
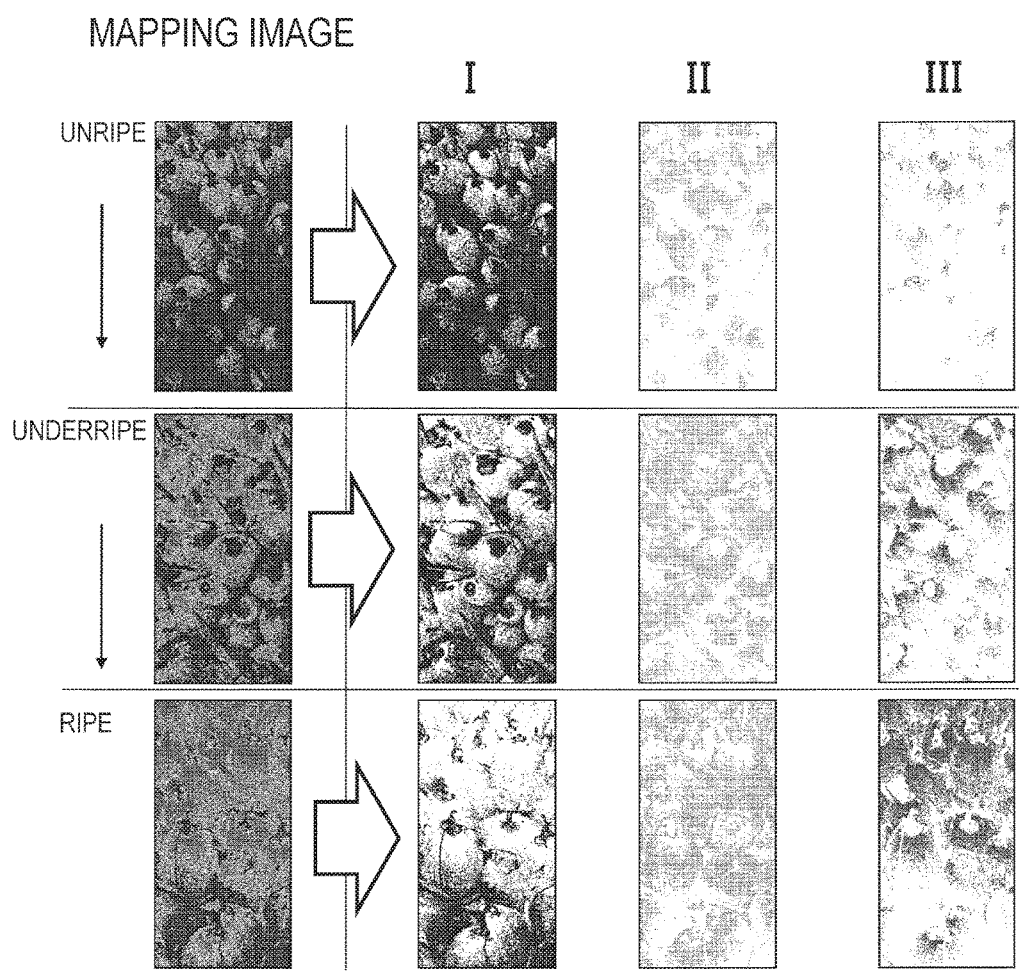
FIG. 15 shows color mapping images obtained as a result of dividing each of three mapping images on the unripe, underripe and ripe bunches F into the three hierarchical layers I, II and III.

FIG. 15 shows color mapping images obtained as a result of dividing each of three mapping images on the unripe, underripe and ripe bunches F into the three hierarchical layers I, II and III, like FIG. 10. The unripe, underripe and ripe bunches F used for maturity determination are the rectangular parts shown in portions (a) of FIG. 9A, FIG. 9B and FIG. 9C. The mapping images shown in FIG. 15 are generated based on a quotient value obtained by dividing the difference value, obtained by subtracting of the pixel value REDS in the image I from the pixel value NIRS, by the pixel value BLUS.

As shown in FIG. 15, regarding the color mapping images of the hierarchical layer I, the density of the pixels (pixel distribution) is highest in the color mapping image on the unripe bunch F and lowest in the color mapping image on the ripe bunch F. Regarding the color mapping images of the hierarchical layer II, the density of the pixels is highest in the color mapping image on the underripe bunch F and lowest in the color mapping image on the unripe bunch F. Regarding the color mapping images of the hierarchical layer III, the density of the pixels is highest in the color mapping image on the ripe bunch F and lowest in the color mapping image on the unripe bunch F.

Figure 16:
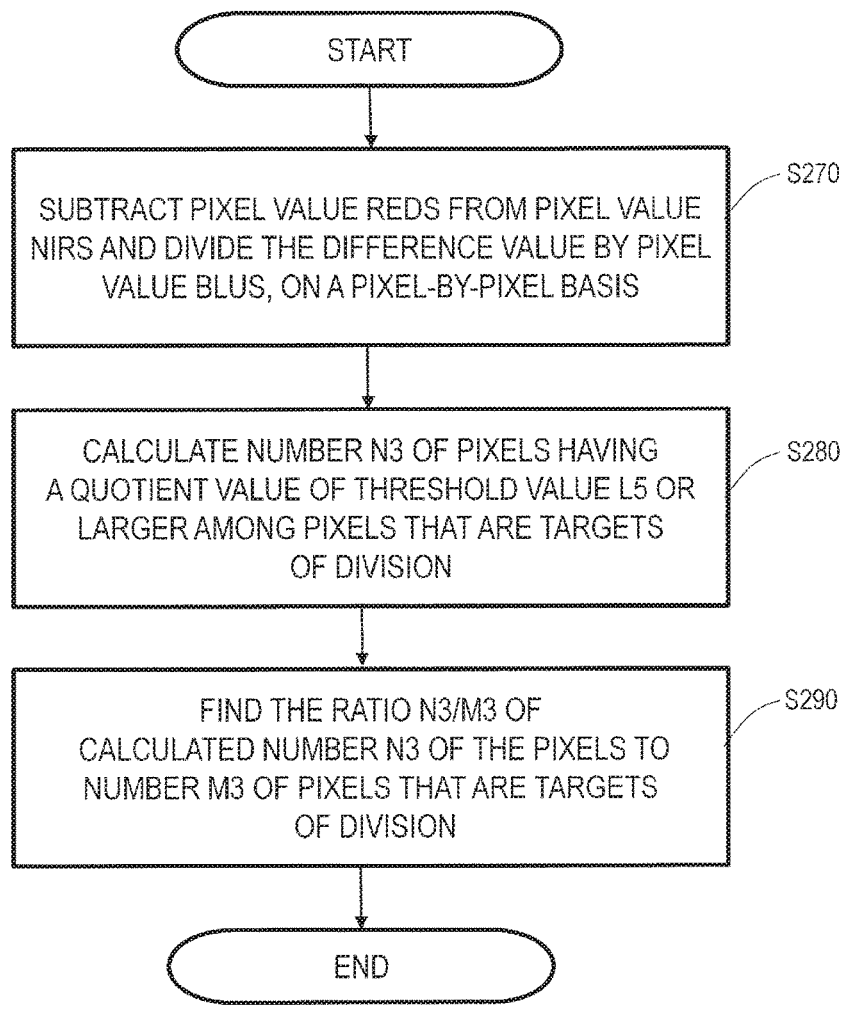
FIG. 16 is a flowchart showing a specific processing procedure in step S200 in embodiment 3 in detail.

FIG. 16 shows a specific processing procedure in step S200 in detail in this embodiment. In step S270, the calculation device P divides, on a pixel-by-pixel basis, the difference value, obtained by subtracting the pixel values REDS obtained from the plurality of third pixels from the pixel values NIRS obtained from the plurality of first pixels on a pixel-by-pixel basis, by the pixel values BLUS obtained from the plurality of second pixels. For example, regarding the pixel unit including the pixels 221 in two rows by two columns shown FIG. 2, the calculation device P subtracts the pixel value REDS obtained from the pixel 221A from the pixel value NIRS obtained from the pixel 221C. The calculation device P divides the resultant difference value by the pixel value BLUS obtained from the pixel 221D.

In step S280, the calculation device P calculates the number N3 of pixels having a quotient value larger than, or equal to, of the threshold value L5 among the pixels that are the targets of division. Typically, the number M3 of the pixels that are the targets of subtraction/division matches the number of the plurality of first pixels. For example, it is assumed that one pixel unit includes two pixels 221C including the IR filter, one pixel 221D including the B filter and one pixel 221A including the R filter. In this case, the pixel value REDS of the pixel 221A may be subtracted from the pixel value NIRS of each of the pixels 221C, and then the resultant difference value may be divided by the pixel value BLUS of the pixel 221D. Alternatively, N3 may be the number of pixels having a quotient value smaller than, or equal to, the threshold value L5, and in step S280, the calculation device P may calculate the number N3 among the pixels that are the targets of division.

In step S290, the calculation device P finds the ratio N3/M3, namely, the ratio of the calculated number N3 of the pixels with respect to the number M3 of the pixels that are the targets of division.

The pixel distribution is represented by the ratio N3/M3, and corresponds to the area size ratio AR, for each hierarchical layer, of the difference between the intensity distributions of the near infrared light and the red light obtained on the basis of the predetermined reference value and in consideration of the intensity distribution of the blue light. For example, the lower limit of the reference value (lower-limit threshold value) and the upper limit of the reference value (upper-limit threshold value) used for the hierarchical layer I are respectively 40 and 50. The lower limit and the upper limit of the reference value used for the hierarchical layer II are respectively 50 and 60. The lower limit of the reference value used for the hierarchical layer III is 60. The upper limit is not set.

Next, the calculation device P follows the processing procedure shown in, for example, FIG. 12A to generate the maturity determination information in accordance with a result of comparing the ratio N3/M3 against a threshold value R5 for each hierarchical layer. Specifically, like in step S310, the calculation device P determines which of the ratio N3/M3 for the hierarchical layer III and the threshold value R5 is larger or smaller. In the case where the ratio N3/M3 is larger than threshold value R5, the calculation device P generates maturity determination information representing "ripe" like in step S320.

With the determination method in this embodiment, the information obtained as a result of subtracting the pixel value REDS from the pixel value NIRS is used, so that the precision of the maturity determination is further improved while the complicated information included in the image I is suppressed.

Embodiment 4

In this embodiment, the calculation device P calculates the number N4 of pixels having a quotient value larger than, or equal to, a threshold value L6 among the pixels that are the targets of division regarding the plurality of third pixels. The calculation device P finds the ratio N4/M4, namely, the ratio of the calculated number N4 of the pixels with respect to the number M4 of the plurality of third pixels. The calculation device P generates maturity determination information based on a result of comparing the ratio N1/M1 against the threshold value R1 and a result of comparing the ratio N4/M4 against a threshold value R6.

Figure 17:
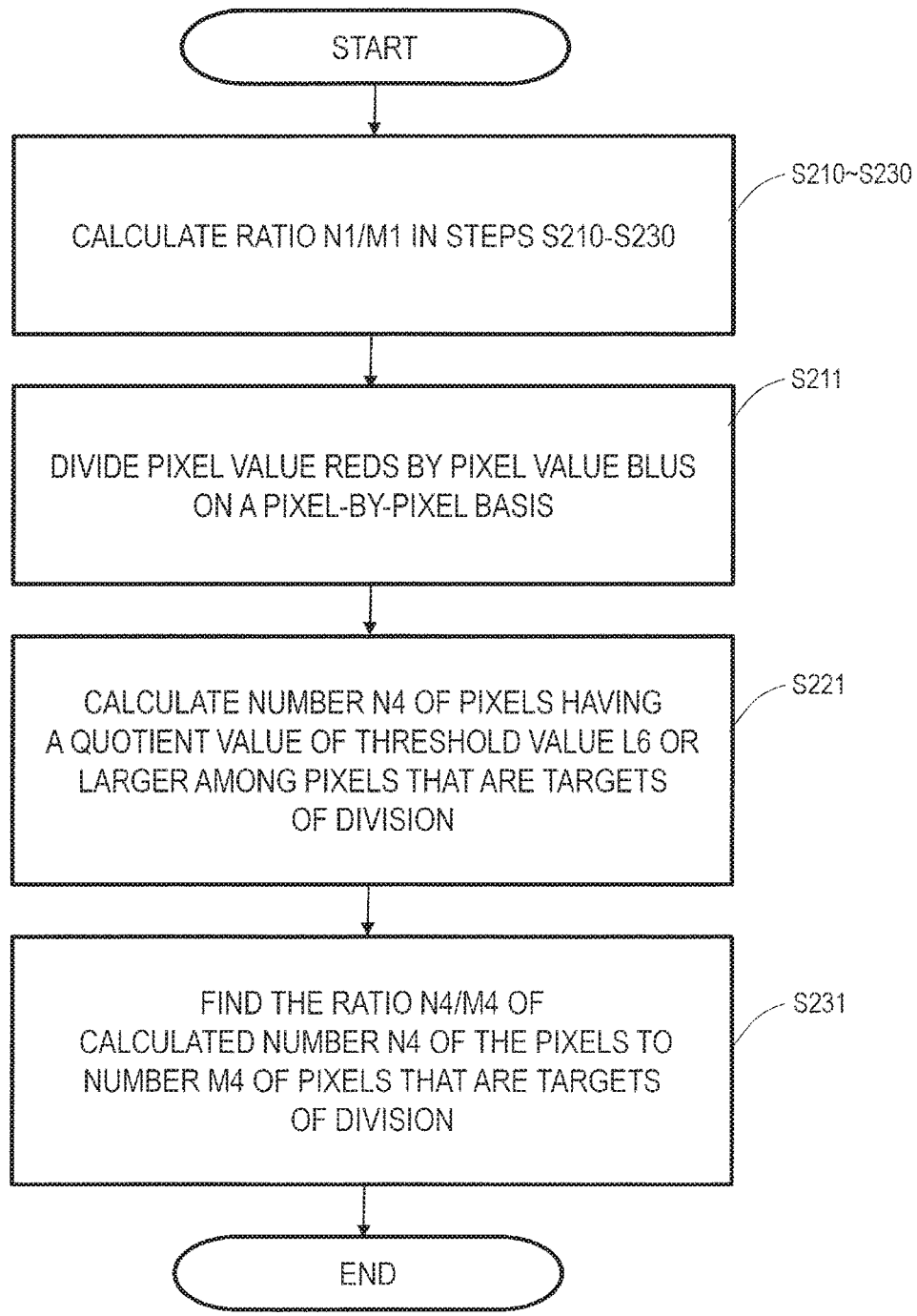
FIG. 17 is a flowchart showing a specific processing procedure in step S200 in embodiment 4 in detail.

FIG. 17 shows a specific processing procedure in step S200 in this embodiment in detail.

First, the calculation device P generates a color mapping image of the hierarchical layer III based on a quotient value obtained by dividing the pixel NIRS in the image I by the pixel value BLUS. Specifically, in steps S210 through S230 shown in FIG. 11, the calculation device P divides the pixel values NIRS by the pixel values BLUS on a pixel-by-pixel basis to calculate the number N1 of pixels having a quotient value larger than, or equal to, the threshold value L1 among the pixels that are the targets of division, and then finds the ratio N1/M1, namely, the ratio of the number N1 of the pixels with respect to the number M1 of the plurality of first pixels.

Next, the calculation device P generates a color mapping image of the hierarchical layer III based on the quotient value obtained by dividing the pixel value REDS in the image I by the pixel value BLUS. Specifically, in steps S211 through S231 shown in FIG. 17, the calculation device P divides the pixel values REDS by the pixel values BLUS on a pixel-by-pixel basis to calculate the number N4 of pixels having a quotient value larger than, or equal to, a threshold value L6 among the pixels that are the targets of division. Then, calculation device P finds the ratio N4/M4, namely, the ratio of the number N4 of the pixels with respect to the number M4 of the plurality of third pixels. Typically, the number of the pixels that are the targets of division matches the number M4 of the plurality of third pixels. For example, for the hierarchical layer III shown in FIG. 10, "80" may be set as the threshold value L6. Namely, as a result of computation, the number of pixels having a pixel value of "80" or larger is N4. Alternatively, N4 may be the number of pixels having a quotient value smaller than, or equal to, the threshold value L6, and in step S221, the calculation device P may calculate the number N4 among the pixels that are the targets of division.

Next, in step S310, the calculation device P checks which of the ratio N1/M1 for the hierarchical layer III and the threshold value R1 is larger or smaller. The calculation device P further checks which of the ratio N4/M4 for the hierarchical layer III and the threshold value R6 is larger or smaller. In the case where the ratio N1/M1 is larger than threshold value R1 and the ratio N4/M4 is larger than threshold value R6, the calculation device P generates maturity determination information representing "ripe" like in step S320.

In this embodiment, in the case where the bunch F cannot be selected as being distinguished from another object, a sensor condition for the pixel value NIRS and a sensor condition for the pixel value REDS are independently set, so that the selectivity of the target is improved.

Embodiment 5

Figure 18:
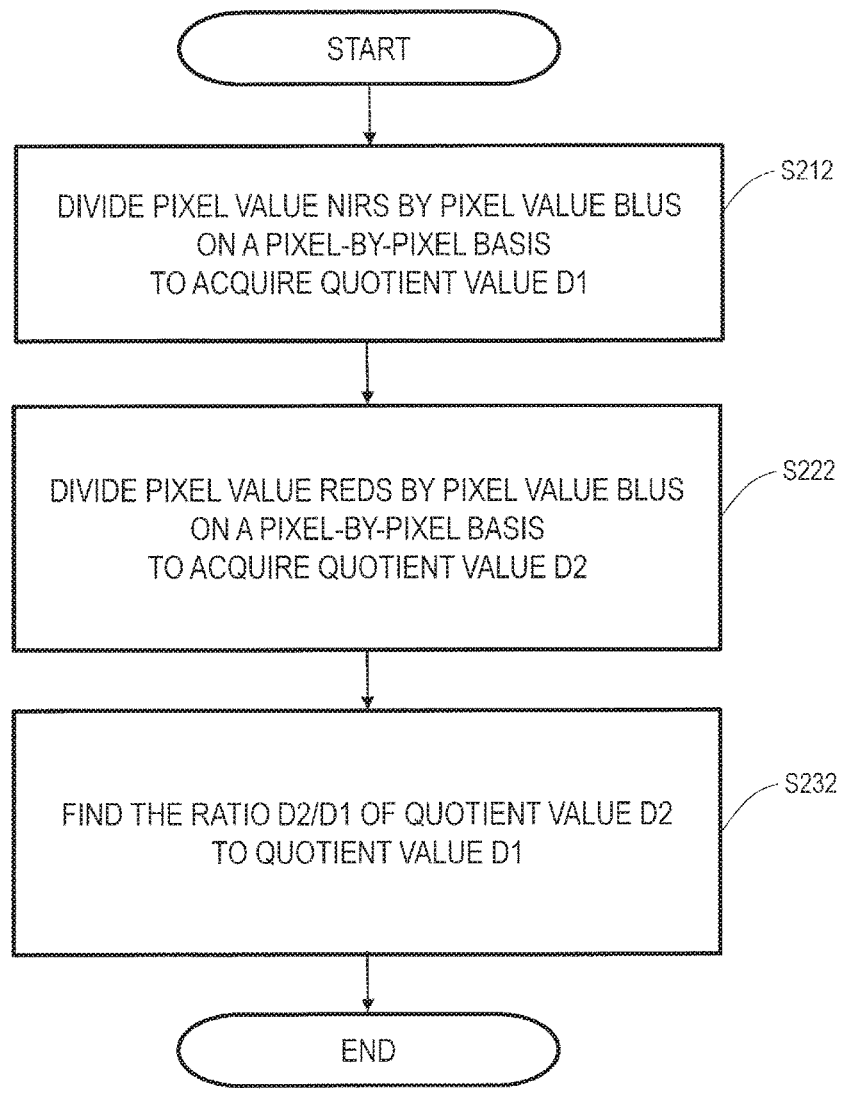
FIG. 18 is a flowchart showing a specific processing procedure in step S200 in embodiment 5 in detail.

FIG. 18 shows a specific processing procedure in step S200 in this embodiment in detail.

In this embodiment, in step S212, the calculation device P divides the pixel values NIRS by the pixel values BLUS on a pixel-by-pixel basis to acquire a quotient value D1, and in step S222, divides the pixel values REDS by the pixel values BLUS on a pixel-by-pixel basis to acquire a quotient value D2. In step S232, the calculation device P finds the ratio D2/D1, namely, the ratio of the quotient value D2 with respect to the quotient value D1. The calculation device P may generate a color mapping image in correspondence with each of the hierarchical layers based on the ratio D2/D1.

Next, in step S310, the calculation device P checks which of the ratio D2/D1 for the hierarchical layer III and the threshold value R7 is larger or smaller. In the case where the ratio D2/D1 is larger than the threshold value R7, the calculation device P generates maturity determination information representing "ripe", like in step S320.

In this embodiment, the amount of change of the pixel value REDS with respect to the pixel value NIRS is found, and the maturity level is finely classified based on the amount of change. As a result, such finely classified maturity levels are visualized.

Embodiment 6

With reference to FIG. 19 through FIG. 22, a structure of a maturity determination device 100 in this embodiment will be mainly described. The maturity determination device 100 is operable in accordance with the processing procedure of the determination method described in each of embodiments 1 through 5.

Figure 19:
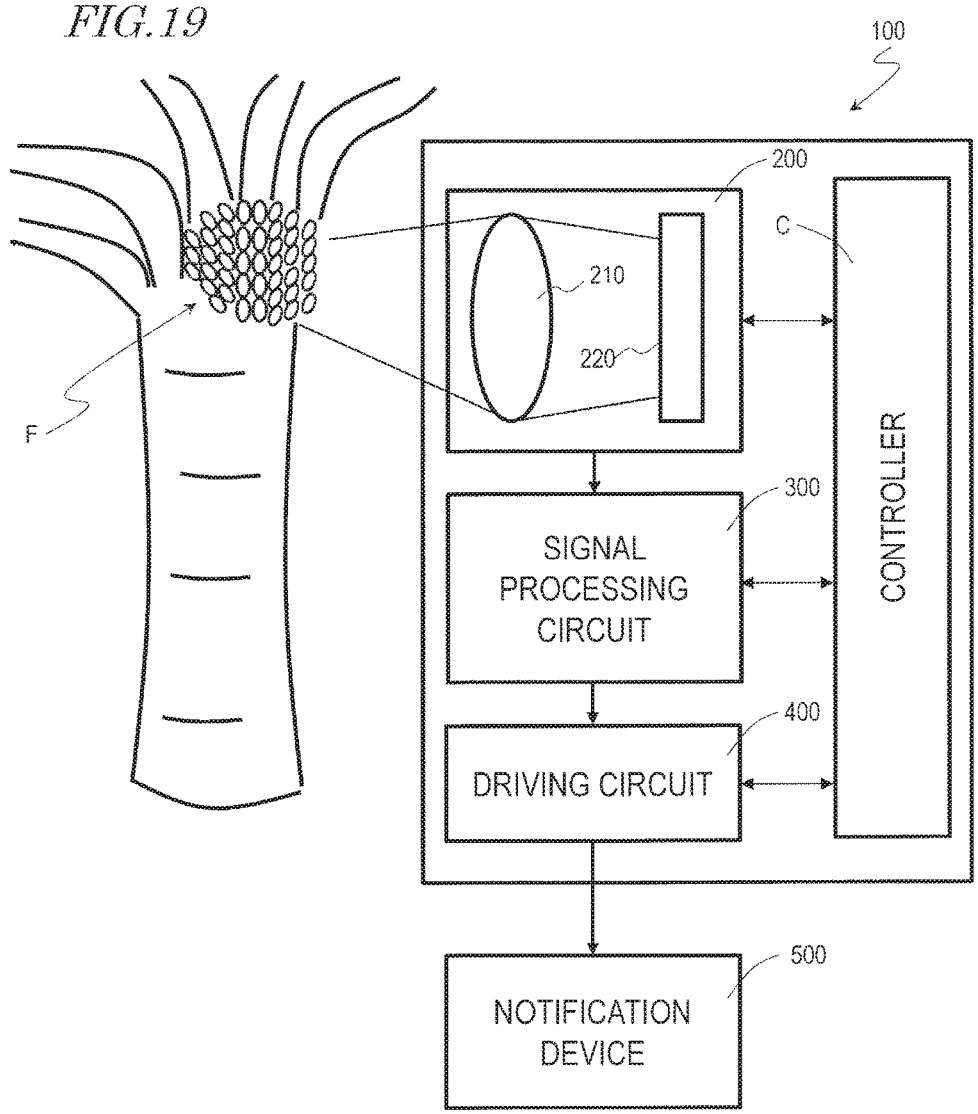
FIG. 19 is a block diagram schematically showing a block structure of a maturity determination device 100.

FIG. 19 schematically shows a block structure of the maturity determination device 100. The maturity determination device 100 typically includes a controller C, an image capturing device 200, a signal calculation device 300 and a driving circuit 400. The maturity determination device 100 is connectable with the notification device 500 in a wired or wireless manner. For example, the maturity determination device 100 may include a USB interface (not shown) and may be connected with the notification device 500 via a USB cable.

The controller C is a semiconductor integrated circuit (LSI), and may be, for example, a general-purpose processor. The controller C is electrically connected with each of the image capturing device 200, the signal processing circuit 300 and the driving circuit 400 to control the entirety of the maturity determination device 100.

The structure of the image capturing device 200 is as described above. As shown in FIG. 2, the image capturing device 200 includes the plurality of pixels 221 arrayed one-dimensionally or two-dimensionally, and performs image capturing of at least a part of the bunch F to acquire the image I. The pixel array 220A is not limited to having the shape shown in FIG. 2, and may have, for example, the shape shown FIG. 5.

Figure 20:
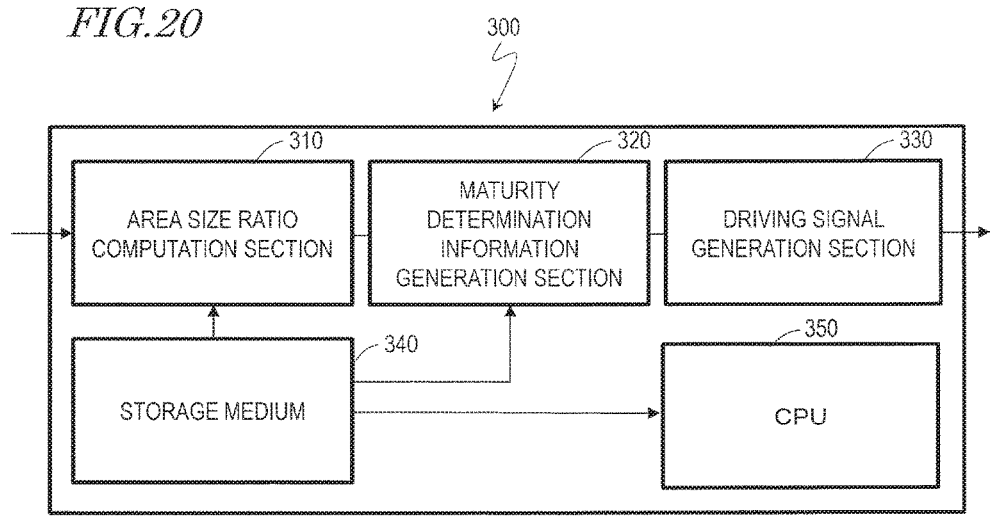
FIG. 20 is a block diagram schematically showing functional blocks of a signal processing circuit 300.

FIG. 20 schematically shows functional blocks of the signal processing circuit 300. Each of the functional blocks of the signal processing circuit 300 is represented on a functional block unit basis, not on a hardware unit basis.

The signal processing circuit 300 is a semiconductor integrated circuit, and is, for example, an image signal processor (ISP). The signal processing circuit of the calculation device P described in embodiment 1 is an element corresponding to the signal processing circuit 300. The signal processing circuit 300 includes an area size ratio computation section 310, a maturity determination information generation section 320, a driving signal generation section 330, a storage medium 340 and a central processing section (CPU) 350. The storage medium 340 is, for example, a read-only memory (ROM), a random access memory (RAM), which is writable, or a hard disc. The area size ratio computation section 310, the maturity determination information generation section 320, and the driving signal generation section 330 may be realized by any combination of hardware and software using, for example, the CPU 350, the RAM (not shown), a computer program loaded on the RAM, the ROM (corresponding to the storage medium 340) storing the computer program, and an interface for connection with a network.

The signal processing circuit 300 includes hardware and/or software, and is configured to operate in accordance with the processing procedure of the determination method described in each of embodiments 1 through 5. For example, the calculation device P (specifically, the signal processing circuit) as the operating subject of the processing procedures of the determination methods shown in FIG. 6, FIG. 11 and FIG. 12A or FIG. 12B may be replaced with the signal processing circuit 300, so that a specific operation of the signal processing circuit 300 is realized. A computer program including a group of commands including such a processing procedure is stored on, for example, the ROM 340. In this embodiment, a description of the operation of the signal processing circuit 300 will be omitted.

Like the calculation device P, the signal processing circuit 300 may generate the color image I of the bunch F based on the pixel values REDS, GLNS and BLUS obtained from the RGB pixels of the image sensor 220. The signal processing circuit 300 may also generate a maturity level image, including information on the reference value and representing the maturity level, based on the maturity determination information. The signal processing circuit 300 may overlap the maturity level image of the color image to generate an overlapping image to be displayed on the notification device 500 (e.g., liquid crystal display). The signal processing circuit 300 may further determine whether the bunch F is harvestable or not based on the maturity determination information.

The driving circuit 400 may include hardware and/or software. The driving circuit 400 is, for example, a semiconductor integrated circuit. The driving circuit 400 generates a driving signal in accordance with the maturity determination information or the determination information on whether the bunch F is harvestable or not in step S400 in the processing procedure shown in FIG. 6. An example of generating a driving signal is described in embodiment 1 in detail.

A part of the maturity determination device 100 may be realized by an LSI as one chip. Each of the functional blocks of the signal processing circuit 300 may be independently a chip. Alternatively, a part of, or the entirety of, the functional blocks of the signal processing circuit 300 may be integrated into a chip. The semiconductor integrated circuit may be, for example, an application specific integrated circuit (ASIC) or a field programmable gate array (FPGA). In the case where a technology of an integrated circuit usable as a substitute of the LSI emerges by the advancement of the semiconductor technology, an integrated circuit realized by such a technology is usable.

Figure 21:
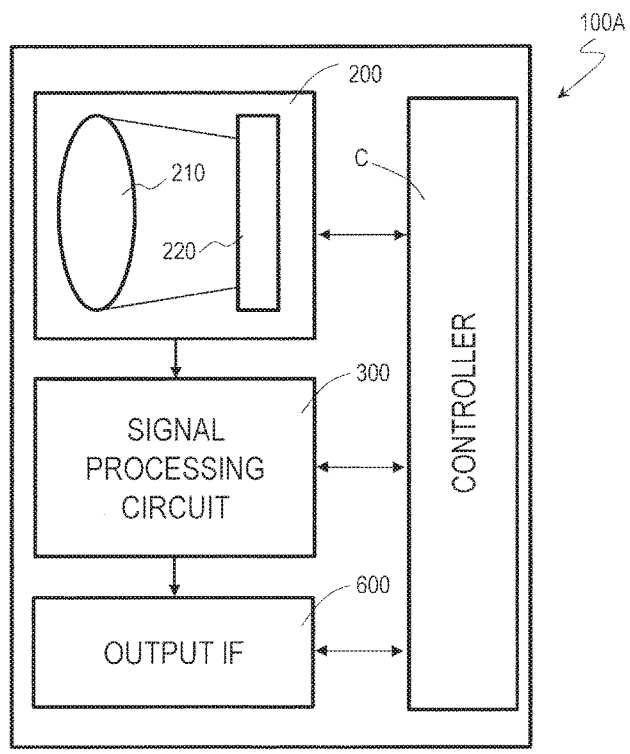
FIG. 21 is a block diagram schematically showing a block structure of a maturity determination device 100A in a variation of embodiment 6.
Figure 22:
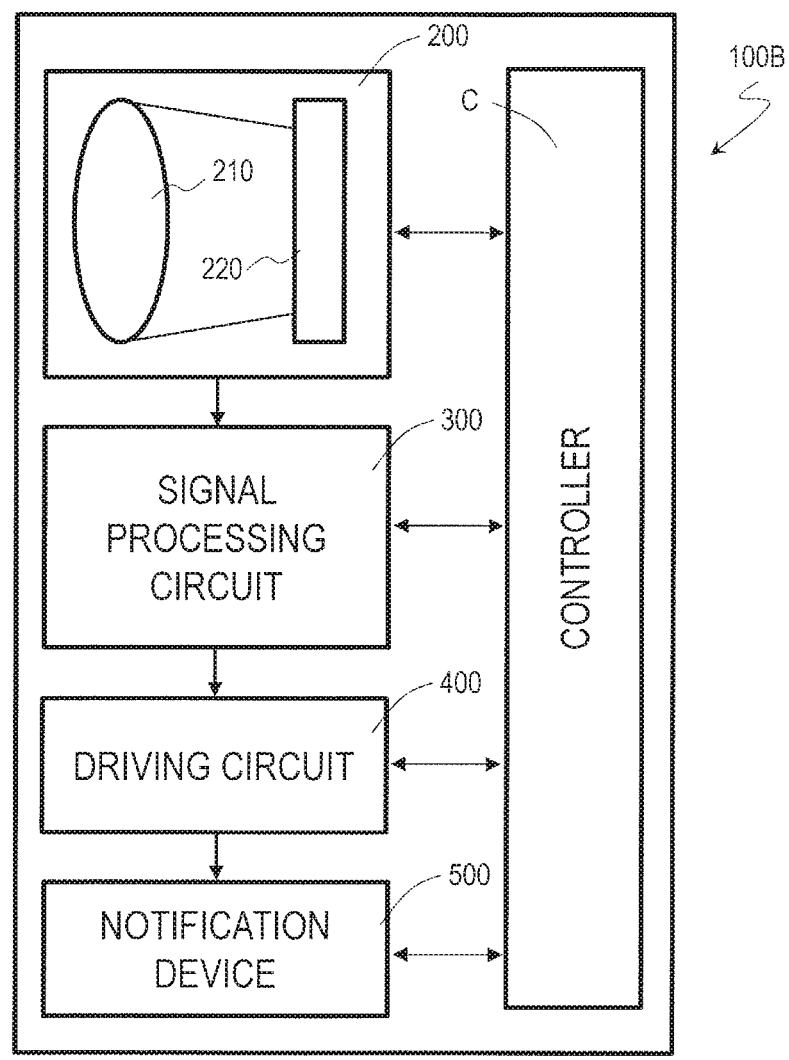
FIG. 22 is a block diagram schematically showing a block structure of a maturity determination device 100B in another variation of embodiment 6.

FIG. 21 schematically shows a block structure of a maturity determination device 100A in a variation of this embodiment. FIG. 22 schematically shows a block structure of a maturity determination device 100B in another variation of this embodiment.

The maturity determination device 100A includes the controller C, the image capturing device 200, the signal processing circuit 300 and an output interface (IF) 600. The maturity determination device 100A includes the output IF 600 instead of the driving circuit 400. The maturity determination device 100A may output the maturity determination information to outside via the output IF 600. The output IF 600 is a USB interface or an interface configured to perform a wireless communication conformed to, for example, the Bluetooth standards. In this variation, in the case where, for example, the notification device 500 has a function of generating a signal for driving the notification device 500 itself, the notification device 500 may receive the maturity determination information from the signal processing circuit 300 and generate a driving signal in accordance with the maturity determination information. The maturity determination device 100A may be provided with a driving circuit as an external element. The driving circuit may receive the maturity determination information and may generate a driving signal in accordance with the maturity determination information.

The maturity determination device 100B includes the controller C, the image capturing device 200, the signal processing circuit 300, the driving circuit 400 and the notification device 500. In this variation, the notification device 500 is integrally included in the maturity determination device 100B. The maturity determination device 100B is decreased in size and thus is easier to use for the farmer.

The signal processing circuit 300 may have a plurality of operation modes respectively operable in accordance with the determination method in each of embodiments 1 through 5. For example, the signal processing circuit 300 may select an optimal operation mode, from the plurality of operation modes, for switching the sensor sensitivity of the image sensor 220 or for narrowing down the sensing results.

In embodiments 1 through 6 described above, the determination method is described regarding an oil palm bunch as an example of fruit or vegetable product, which is a harvesting target. The fruit or vegetable product targeted by the present invention is not limited to the oil palm bunch, and may be any fruit or vegetable product having a reflectance characteristic of the near infrared light that the reflectance varies in accordance with the maturity level. An example of such a fruit or vegetable product is, for example, green apple or mango.

Figure 23A:
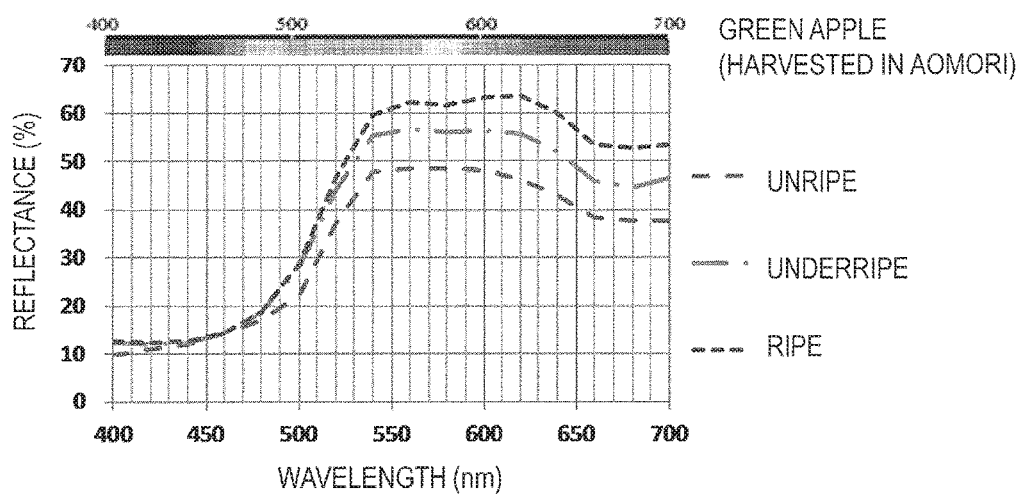
FIG. 23A is a graph showing the wavelength dependence of the reflectance of light reflected by green apple.
Figure 23B:
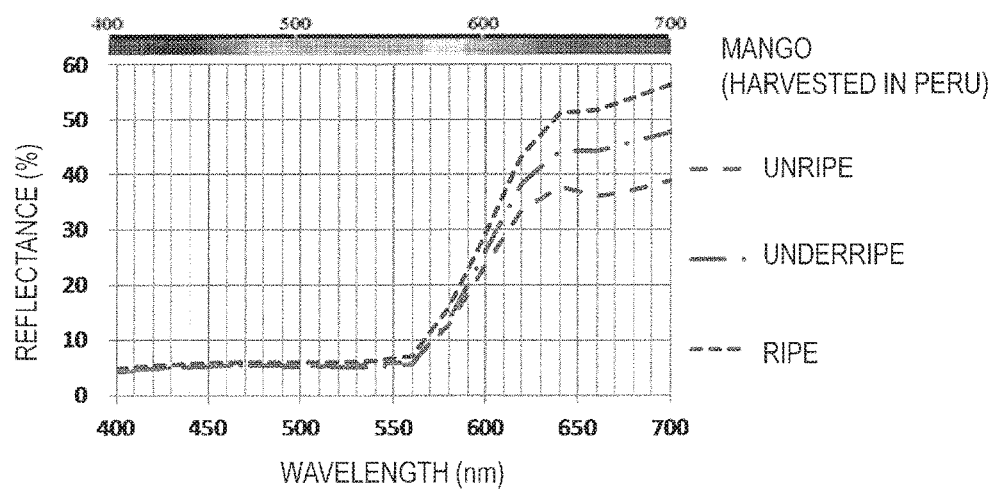
FIG. 23B is a graph showing the wavelength dependence of the reflectance of light reflected by mango.

FIG. 23A shows an example of wavelength dependence of the reflectance of light by green apple. FIG. 23B shows an example of wavelength dependence of the reflectance of light by mango. The horizontal axis represents the wavelength (nm) of the light, and the vertical axis represents the reflectance (%). Like in the case of the oil palm bunch F, the reflectance tends to increase as the maturity level rises especially in the wavelength band of the red light. It is seen that also in the wavelength band of the near infrared light, the reflectance tends to increase as the maturity level rises. Therefore, an embodiment of the present invention is preferably applicable to green apple and mango. Substantially the same effects are provided as for the oil palm bunch F. The target of determination of an embodiment of the present invention is not limited to the maturity level, and may be any of other indexes by which the time to harvest may be learned (e.g., growing degree, freshness, harvest level, etc.).

The determination method in an embodiment according to the present invention may be realized by a computer program. The computer program is configured to realize the various functions described above in embodiments 1 through 5. The computer program controls, for example, the calculation device P and the CPU or the like of the maturity determination device 100. Information handled by these devices is temporarily stored on the RAM when being processed, and then is stored on any of various ROMs or HDDs. The CPU reads the information when necessary, and corrects the information or write additional data on the information. The storage medium storing the computer program may be, for example, a semiconductor storage medium (e.g., ROM, nonvolatile memory card, etc.), an optical storage medium (e.g., DVD, MO, MD, CD, BD, etc.), a magnetic storage medium (e.g., magnetic tape, flexible disc, etc.) or the like. Each of the functions described above in embodiments 1 through 5 is realized by the CPU loading and executing the computer program. Alternatively, each of the functions described above in embodiments 1 through 5 may be realized by the CPU in cooperation with an operating system, another application program or the like in accordance with an instruction of the computer program.

The computer program may be stored on a portable storage medium, so that the contents thereof are distributed in the market. Alternatively, the computer program may be transferred to a server computer connected via a network such as the Internet or the like, so that the contents thereof are distributed in the market. In this case, the storage device included in the server computer is encompassed in the present invention. Each of the functions described above in embodiments 1 through 5 may be stored on a computer-readable medium, or transferred, as at least one command group or a code. The "computer-readable storage medium" encompasses a communication medium including a medium assisting the computer program be carried from one site to another site and also encompasses a computer storage medium. The storage medium may be any commercially available medium accessible by a general-purpose computer or a special-purpose computer.

In this specification, various illustrative elements, blocks, modules, circuits and steps are described generally regarding the functionality thereof in order to clearly show the synonymy between hardware and software. Whether such functionality is implemented as hardware or software depends on the designing restriction imposed on each of applications and the entire system. A person of ordinary skill in the art could implement the functions by any of various methods for specific applications, but determination on such implementation should not be construed as departing from the scope of this disclosure.

Various illustrative logical blocks and processing units described in relation with the disclosure of this specification may be implemented or executed by a general-purpose processor, a digital signal processor (DSP), an ASIC, an FPGA, any other programmable logical device, a discrete gate or transistor logic, or a discrete hardware component designed to execute the functions described in this specification, or a combination of any of these. The general-purpose processor may be a microprocessor, or may be a conventional processor, controller, microcontroller or state machine. The processor may be implemented by a combination of computing devices. For example, the processor may be realized by a combination of a DSP and a microprocessor, a combination of a plurality of microprocessors, a combination of a DSP core and at least one microprocessor connected with the DSP core, or a combination of any other such devices.

The determination methods or the steps of algorithm described in relation with the disclosure of this specification may be directly embodied by a software module executable by hardware (especially, a processor) or by a combination of hardware and the software module. The software module may be present in a RAM, a flash memory, a ROM, an EPROM, an EEPROM, a register, a hard disc, a removable disc, a CD-ROM, or any storage medium in any form known in this field. A typical storage medium may be coupled to the processor such that information may be read therefrom, or written thereto, by the processor. With another method, the storage medium may be integrated with the processor. The processor and the storage medium may be in the ASIC. The ASIC may be mounted on the maturity determination device. Alternatively, the processor and the storage medium may be housed in the maturity determination device as discrete elements.

Embodiments of the present invention have been described in detail with reference to the drawings. Specific structures are not limited to any of the embodiments, and designs and the like not departing from the gist of the present invention are encompassed in the scope of the claims.

A maturity determination method and a maturity determination device in an embodiment according to the present invention are preferably usable for a method and a device determining the maturity level of a fruit or vegetable product, especially the maturity level of a bunch including a large number of fruits.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A maturity determination device determining a maturity level of a fruit or vegetable product, comprising:
    an image capturing device including a plurality of pixels arrayed one-dimensionally or two-dimensionally, the image capturing device performing image capturing of at least a part of the fruit or vegetable product to acquire an image, the plurality of pixels including a plurality of first pixels each including a first light transmission filter selectively transmitting light of a first wavelength band and a plurality of second pixels each including a second light transmission filter selectively transmitting light of a second wavelength band, the intensity of the light of the first wavelength band reflected by the fruit or vegetable product varying in accordance with the maturity level, and the intensity of the light of the second wavelength band reflected by the fruit or vegetable product being substantially the same regardless of the maturity level; and
    a signal processing circuit configured to find an area size ratio of an intensity distribution of the light of the first wavelength band on the basis of a predetermined reference value based on pixel values obtained from the plurality of first pixels and the plurality of second pixels, and to generate maturity determination information in accordance with the area size ratio.

2. The maturity determination device according to claim 1, wherein the first wavelength band is a wavelength band of near infrared light.

3. The maturity determination device according to claim 2, wherein the first wavelength band is a wavelength band of near infrared light from 800 nm to 900 nm.

4. The maturity determination device according to claim 1, wherein the second wavelength band is a wavelength band of blue light.

5. The maturity determination device according to claim 1, wherein the signal processing circuit:
    divides, on a pixel-by-pixel basis, the pixel values obtained from the plurality of first pixels by the pixel values obtained from the plurality of second pixels associated with the plurality of first pixels;
    calculates the number of pixels having a quotient value larger than, or equal to, a first threshold value, or a quotient value smaller than, or equal to, the first threshold value, among pixels that are targets of division to find a first ratio of the calculated number of the pixels with respect to the number of the plurality of first pixels; and
    generates the maturity determination information in accordance with a result of comparing the first ratio against a second threshold value.

6. The maturity determination device according to claim 1, wherein:
    the plurality of pixels further include a plurality of third pixels each including a third light transmission filter selectively transmitting light of a third wavelength band, the intensity of the light of the third wavelength band reflected by the fruit or vegetable product varying in accordance with the maturity level, the third wavelength band being different from the first wavelength band; and
    the signal processing circuit generates the maturity determination information based on pixel values obtained from the plurality of first, second and third pixels.

7. The maturity determination device according to claim 6, wherein the third wavelength band is a wavelength band of red light.

8. The maturity determination device according to claim 6, wherein the plurality of first, second and third pixels are associated with each other.

9. The maturity determination device according to claim 8, wherein the signal processing circuit:
    divides, on a pixel-by-pixel basis, sum values, obtained by adding the pixel values obtained from the plurality of first pixels and the pixel values obtained from the plurality of third pixels on a pixel-by-pixel basis, by the pixel values obtained from the plurality of second pixels;
    calculates the number of pixels having a quotient value larger than, or equal to, a first threshold value, or a quotient value smaller than, or equal to, the first threshold value, among pixels that are targets of division to find a first ratio of the calculated number of the pixels with respect to the number of the pixels that are the targets of division; and
    generates the maturity determination information in accordance with a result of comparing the first ratio against a second threshold value.

10. The maturity determination device according to claim 8, wherein the signal processing circuit:
    divides, on a pixel-by-pixel basis, difference values, obtained by subtracting the pixel values obtained from the plurality of third pixels from the pixel values obtained from the plurality of first pixels on a pixel-by-pixel basis, by the pixel values obtained from the plurality of second pixels;
    calculates the number of pixels having a quotient value larger than, or equal to, a first threshold value, or a quotient value smaller than, or equal to, the first threshold value, among pixels that are targets of division to find a first ratio of the calculated number of the pixels with respect to the number of the pixels that are the targets of division; and
    generates the maturity determination information in accordance with a result of comparing the first ratio against a second threshold value.

11. The maturity determination device according to claim 8, wherein the signal processing circuit:
    divides, on a pixel-by-pixel basis, the pixel values obtained from the plurality of first pixels by the pixel values obtained from the plurality of second pixels;
    calculates the number of pixels having a quotient value larger than, or equal to, a first threshold value, or a quotient value smaller than, or equal to, the first threshold value, among pixels that are targets of division to find a first ratio of the calculated number of the pixels with respect to the number of the plurality of first pixels;
    divides, on a pixel-by-pixel basis, the pixel values obtained from the plurality of third pixels by the pixel values obtained from the plurality of second pixels;
    calculates the number of pixels having a quotient value larger than, or equal to, a second threshold value, or a quotient value smaller than, or equal to, the second threshold value, among the pixels that are the targets of division to find a second ratio of the calculated number of the pixels with respect to the number of the plurality of third pixels; and generates the maturity determination information in accordance with a result of comparing the first ratio against a third threshold value and a result of comparing the second ratio against a fourth threshold value.

12. The maturity determination device according to claim 8, wherein the signal processing circuit:
- divides, on a pixel-by-pixel basis, the pixel values obtained from the plurality of first pixels by the pixel values obtained from the plurality of second pixels to find a first quotient value;
- divides, on a pixel-by-pixel basis, the pixel values obtained from the plurality of third pixels by the pixel values obtained from the plurality of second pixels to find a second quotient value;
- calculates, on a pixel-by-pixel basis, a third ratio of the second quotient value with respect to the first quotient value; and
- generates the maturity determination information in accordance with a result of comparing the third ratio against a fifth threshold value.

13. The maturity determination device according to claim 6, wherein:
- the plurality of pixels further include a plurality of fourth pixels each including a fourth light transmission filter selectively transmitting green light, the second wavelength band being a wavelength band of blue light and the third wavelength band being a wavelength band of red light; and
- the signal processing circuit generates a color image based on pixel values obtained from the plurality of second, third and fourth pixels, and generates, based on the maturity determination information, a maturity level image including information on the reference value and representing the maturity level.

14. The maturity determination device according to claim 1, further comprising an output interface outputting the maturity determination information to outside.

15. The maturity determination device according to claim 1, further comprising a driving circuit which generates a driving signal for driving a notification device notifying the maturity level, the notification device being connectable with the maturity determination device, and the driving signal being generated in accordance with the maturity determination information.

16. The maturity determination device according to claim 1, further comprising:
- a notification device which notifies the maturity level; and
- a driving circuit which generates a driving signal for driving the notification device, the driving signal being generated in accordance with the maturity determination information.

17. The maturity determination device according to claim 13, further comprising:
- a display device; and
- a driving circuit which generates a driving signal for driving the display device, the driving signal being generated in accordance with the maturity determination information;
- wherein the display device displays the maturity level image as overlapping the color image in accordance with the driving signal.

18. The maturity determination device according to claim 1, wherein the signal processing circuit determines whether the fruit or vegetable product is harvestable or not based on the maturity determination information.

19. The maturity determination device according to claim 1, wherein the light reflected by the fruit or vegetable product at the time of harvest thereof has an optical characteristic that an intensity thereof increases as the light has a longer wavelength in a wavelength band from blue light to near infrared light.

20. The maturity determination device according to claim 1, wherein the fruit or vegetable product is a bunch with a large number of fruits.

* * * * *